(12) United States Patent
Yamazaki et al.

(10) Patent No.: US 6,426,395 B1
(45) Date of Patent: Jul. 30, 2002

(54) μ-OXO-BIS-METALLOCENE COMPLEX COMPOUNDS AND CATALYSTS USING SAME FOR THE POLYMERIZATION OF OLEFINS AS WELL AS POLYMERIZATION PROCESS

(75) Inventors: Hiroshi Yamazaki, 41-10, Matsugaoka 2-chome, Tokorozawa, Saitama-ken 359-1132; Masato Nakano, Chiba; Seiki Mitani, Yokohama; Jun Saito, Kimitsu; Masato Harada, Yokohama; Mina Koyama, Tokyo, all of (JP)

(73) Assignees: Chisso Corporation, Tokyo; Hiroshi Yamazaki, Saitama, both of (JP)

( * ) Notice: Subject to any disclaimer, the term of this patent is extended or adjusted under 35 U.S.C. 154(b) by 0 days.

(21) Appl. No.: 09/509,742

(22) PCT Filed: Feb. 8, 1999

(86) PCT No.: PCT/JP99/04147

§ 371 (c)(1),
(2), (4) Date: May 22, 2000

(87) PCT Pub. No.: WO00/08036

PCT Pub. Date: Feb. 17, 2000

(30) Foreign Application Priority Data

Aug. 3, 1998 (JP) ............................................. 10-218731
Aug. 3, 1998 (JP) ............................................. 10-218732

(51) Int. Cl.$^7$ ............................. C08F 4/44; B01J 31/38
(52) U.S. Cl. ...................... 526/160; 526/127; 526/943; 556/53; 502/152
(58) Field of Search ................................ 526/160, 161, 526/943; 502/152; 556/53

(56) References Cited

PUBLICATIONS

Nakano et al., Synthesis of u–oxo complexes of Group 4 bridged–metallocenes, Chemistry Letters, Nov. 1998, pp. 1139–1140.*

Royo et al., Dicyclopentadienyl titanium and zirconium complexes with the double bridged bis(dimethysilanodyl) dicyclopentadieniyl, JOMC 526 (1996) 227–235.*

* cited by examiner

*Primary Examiner*—David W. Wu
*Assistant Examiner*—R. Harlan
(74) *Attorney, Agent, or Firm*—Leydig, Voit & Mayer, Ltd.

(57) ABSTRACT

Disclosed are μ-oxo-bis-metallocene complex compounds, catalysts for the polymerization of olefins comprising a μ-oxo-bis-metallocene complex compound and at lease one cocatalyst selected from the group consisting of an aluminoxane, an ionic compound, and a Lewis acid, and a process for the polymerization of olefins. An example of the μ-oxo-bis-metallocene complex compound is represented by the following formula (1):

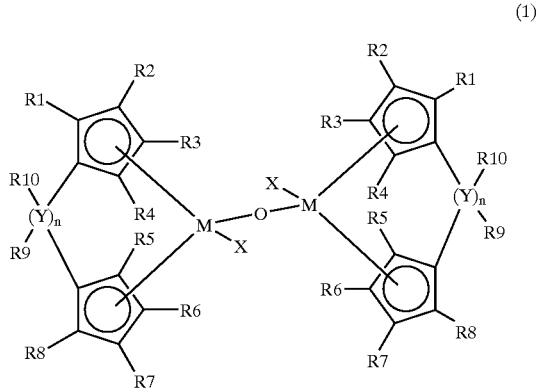

(1)

wherein, for example, M is zirconium, n is 1, Y is silicon, X is chloro, and R1–R10 maybe hydrogen or alkyl.

12 Claims, 2 Drawing Sheets

μ-OXO-BIS-METALLOCENE COMPLEX COMPOUNDS AND CATALYSTS USING SAME FOR THE POLYMERIZATION OF OLEFINS AS WELL AS POLYMERIZATION PROCESS

TECNICAL FIELD

The present invention relates to μ-oxo-bis-metallocene complex compounds and catalysts using same for the polymerization of olefins as well as polymerization processes. In particular, the present invention is featured by using as the metallocene complex compounds those having cyclopentadienyl rings, especially a bridged cyclopentadienyl ligand.

BACKGROUND ART

It is known that a variety of metallocene complex compounds are proposed as a component for the polymerization of olefins and that various olefin polymers can be produced by selecting the sort of metallocene complex compounds. Especially in the polymerization of propylene, it is publicly known that any of the atactic polypropylene, isotactic polypropylene and syndiotactic polypropylene can be produced. (Makromol. Chem., Rapid. Commun. 1983, 4,417–421; Angew. Chem., Int. Engl. 1985, 24, 507–508; J. Am. Chem. Soc. 1988, 110, 6255–6256; etc.) Purification of metallocene complex compounds is usually carried out by washing, extraction with a solvent, recrystallization and the like means. However, a considerable amount of metallocene complex compounds remain in a residue after purification, e.g. in washing liquids and a mother liquid of recrystallization, and the metallocene complex compounds cannot be recovered in some cases so that it incurs economical disadvantage.

Depending on the positions of substituents at the time of synthesis, metallocene complexes may permit the existence of stereoisomers. In the event a mixture of complex isomers formed on synthesis is straightforwardly used for polymerization of olefins where different olefin polymers are produced according to the different nature of the isomers, the resultant polymer will become a mixture of two different polymers. In case a uniform polymer is to be produced, therefore, the mixture of polymers has to be separated. For obtaining a highly pure isomeric form, however, repeating of the separation operations was necessary so that efficiency of the production was extremely low.

In Japanese Laid-open Patent Appln. No. Hei. 10-67793, there is disclosed that a method of changing the racemic/meso ratio wherein unnecessary isomer is decomposed with a decomposing agent such as acidic hydrogen atom or a reactive halogen atom. This method pertains to changing of the racemic/meso ratio by decomposing either one of the isomers, and more precisely, the racemic form is decomposed with ethylene-bis(4,7-dimethylindenyl)zirconium dichloride to obtain the pure meso form. As the other isomer is decomposed, however, this decomposed isomer cannot be used as catalyst component so that this method is regarded economically less interested.

A number of references are known concerning μ-oxo-bis-metallocene complex compounds having non-bridged cyclopentadienyl ligans, for example, Inorganic Chemistry 15, No. 9, 1976 disclosing that dimethylhafnocene is brought into contact with water in the air to form μ-oxo-bis (methylhafnocene) and Comprehensive Organometallic Chemistry 4, 1982, 527–528 disclosing a μ-oxo-complex compound containing a briged ligand.

In addition, Japanese laid-open Patent Appln. No. Hei. 7-233211 discloses a catalyst for the polymerization of olefins which contains a μ-oxo-complex combining metals of two nuclear complexes bridging Cp.

TECHNICAL PROBLEMS OF THE INVENTION

It is an object of the present invention to provide a novel μ-oxo-bis-metallocene complex compound excellent in crystallinity and separability and capable of being used as a catalyst component for the polymerization of olefins.

It is another object of the present invention to provide a catalyst for the polymerization of olefins which comprises the aforesaid novel μ-oxo-bis-metallocene complex compound.

It is still another object of the present invention to provide a process for polymerizing olefins by the aid of the above catalyst.

As a result of extensive research made to attain the aforesaid objects, it has now been found that μ-oxo-bis-metallocene complex compounds having an M—O—M bond are excellent in crystallinity and easily capable of being isolated from a reaction liquid at the time of synthesis and can be employed as a catalyst component for the polymerization of olefins. The present invention has been accomplished on the basis of the above finding.

DISCLOSURE OF THE INVENTION

According to the present invention, there is provided a μ-oxo-bis-metallocene complex compound represented by the formula (1):

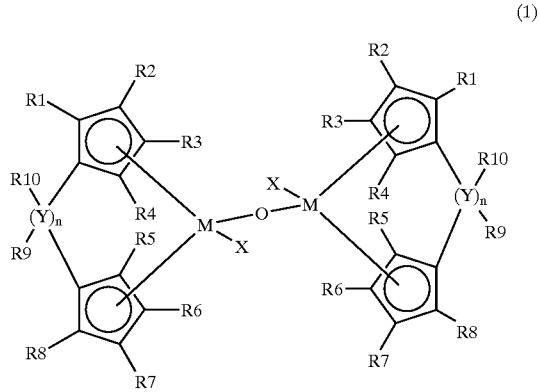

(1)

wherein M stands for a transition metal belonging to Group III, IV, V, VI, Lantanoid or Actinoid of the Periodic Table, n stands for an integer of 1 or 2, Y stands for carbon, silicon, germanium or tin, X's may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or- nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings by other substituents with the proviso that the adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R1–R8 are not hydrogen at the same time.

According to the present invention, there is also provided the aforesaid μ-oxo-bis-metallocene complex compound wherein R2, R3, R6 and R7 in the above formula (1) are not hydrogen at the same time.

According to the present invention, there is further provided the aforesaid μ-oxo-bis-metallocene complex compound wherein M and Y in the above formula (1) each stands for titanium, zirconium or hafnium and for carbon, silicon or germanium, respectively.

According to the present invention, there is still another provided a μ-oxo-bis-metallocene complex compound represented by the formula (2):

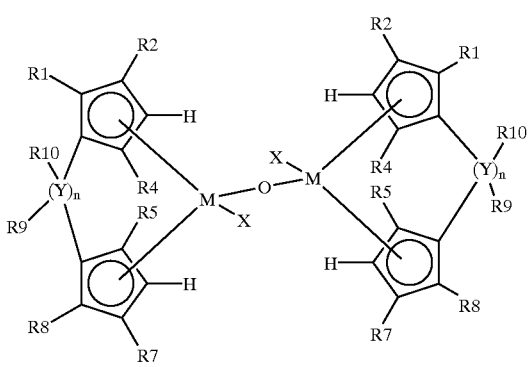

(2)

wherein M stands for titanium, zirconium, or hafnium, n stands for an integer of 1 or 2, Y stands for carbon, silicon, or germanium, X's may be the same or different and: each independently stands for a halogen atom, a halogenoid atomic group, a hydrocarbon group hang 1–20 carbon atoms which may contain silicon, germanium, oxygen, sulfur or nitrogen, or a monocyclic heteroaromatic group which may contain a hetero atom or atoms selected. from the group consisting of oxygen atoms, sulfur atoms and nitrogen atoms in the 5-membered or 6-membered ring or rings. thereof and which may be substituted on the ring or rings thereof by other substituents, R1, R2, R4, R5, R7 and R8 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings by other substituents with the proviso that R1 and R2 may form together a cyclic structure having 5–8 carbon atoms and the cyclic structure may be an aromatic ring, that R7 and R8 may form a cyclic structure having 4–8 carbon atoms and which may contain oxygen, sulfur and nitrogen, and that R1, R2, R4, R5, R7 and R8 are not hydrogen at the same time.

According to the present invention, there is still further provided the aforesaid μ-oxo-bis-metallocene complex compound wherein R2 and R7 in the above formula (2) are substituents other than hydrogen in which ligands coordinated to the two M's are commonly in meso position.

According to the present invention, there is still further provided a catalyst for the polymerization of olefins which comprises, as essential components thereof, at least one of the μ-oxo-bis-metallocene complex compound represented by the formula (1) (the component A) and at least one of the cocatalyst selected from the group consisting of (a) an aluminoxane, (b) an ionic compound and (c) a Lewis acid (the component B).

According to the present invention, there is still further provided the aforesaid catalyst for the polymerization of olefins wherein the component A is a μ-oxo-bis-metallocene complex compound represented by the formula (1) in which M is titanium, zirconium or hafnium, Y is carbon, silicon or germanium.

According to the present invention, there is still further provided the aforesaid catalyst for the polymerization of olefins wherein the component A is a μ-oxo-bis-metallocene complex compound represented by the. formula (2).

According to the present invention, there is still further provided the aforesaid catalyst for the polymerization of olefins wherein the component B is (a) an aluminoxane.

According to the present invention. there is yet further provided a process for the polymerization of olefins in the presence of the aforesaid catalyst for the polymerization of olefins.

A BEST EMBODIMENT FOR CARRYING OUT THE INVENTION

Figure 1:
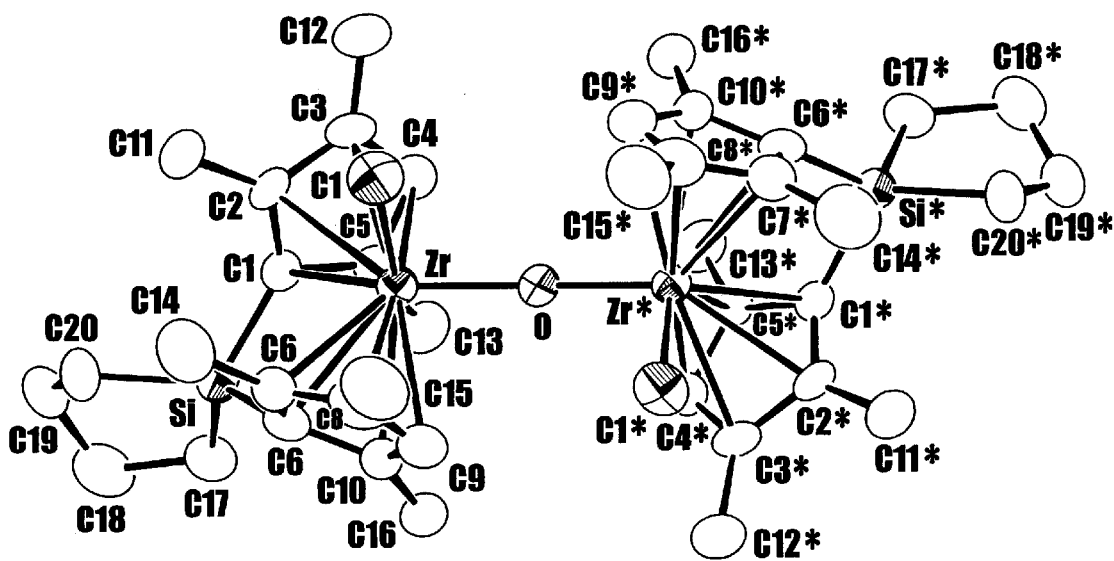
FIG. 1 is an ORTEP drawing obtained accpording to a single-crystal X-ray diffraction of μ-oxo-bis[silacyclopantane-bis(2,3,5-trimethylcyclopentadienyl) zirconium chloride].
Figure 2:
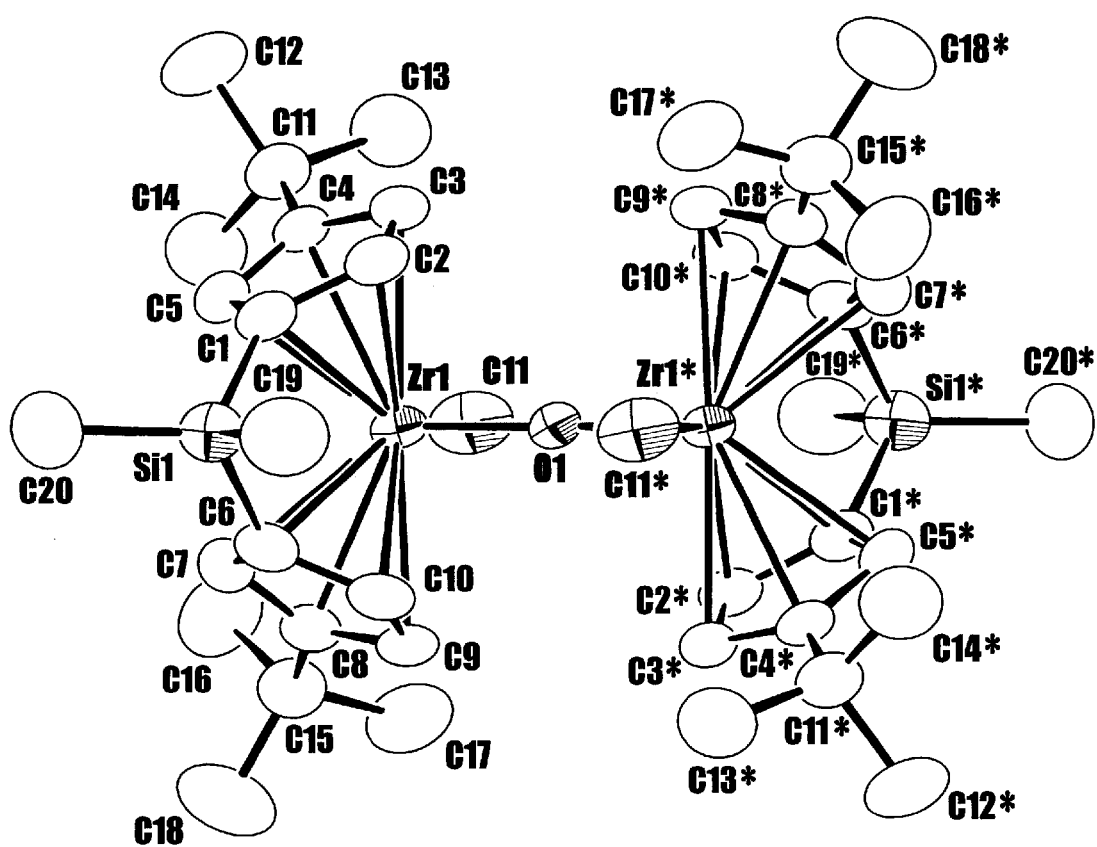
FIG. 2 is an ORTEP drawing obtained according to a single-crystal X-ray diffraction of μ-oxo-bis[dimethylsilylene-bis(3-tert-butylcyclopentadienyl) zirconium chloride].

A maximum characteristic feature of the μ-oxo-bis-metallocene complex compounds resides in constituting the cyclopentadienyl ring as ligand, especially in having the bridged cyclopentadienyl ligand in the structure.

This μ-oxo-bis-metallocene complex compound is useful as a catalyst for the production of polyolefins having a narrow molecular weight distribution when used together with the undermentioned cocatalyst to form a highly active catalyst for the polymerization of olefins.

Below is a detailed description on the construction and effect of the present invention.

μ-Oxo-bis-metallocene complex compounds of the present invention are those represented by the formula (1).

In this formula, M stands for a transition metal belonging to Group III, IV, V, VI and Lantanoid and Actinoid of the Periodic Table, preferably titanium, zirconium, or hafnium belonging to Group IV. Y stands for carbon, silicon, germanium, and tin. preferably carbon silicon and germanium. The substituents X's on the zirconium may be the same or different and each independently stands for a halogen atom, a halogenoid atomic group or a hydrocarbon group having 1–20 carbon atoms or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings by other substituents. Examples of the halogen include fluorine, chlorine, bromine and iodine. Preferable is chlorine, bromine and iodine. Examples of the halogenoid atomic group include the grouping of NCS, NCO, N$_3$, N(CN)$_2$, C(CN)$_3$, C(CN)$_2$, and (NO). Examples of the hydrocarbon group having 1–20 carbon atoms include an alkyl group, a cycloalkyl group, an aryl group, an alkylaryl and an aralkyl group. Examples of the heteroaromatic group include furyl group, thienyl group and pyridyl group.

The substituents R1, R2, R3, R4, R5, R6, R7, R8, R9, and R10 may be the same or different and each independently stands for hydrogen, an alkyl group having having 1–20 carbon atoms, a cycloalkyl group having 3–20 carbon atoms, an alkenyl group having a 2–20 carbon atoms, an aryl group having 6–20 carbon atoms, an alkylaryl group having 7–20 carbon atoms, an aralkyl group having 7–20 carbon atoms which may contain oxygen, sulfur and nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents. Illustrative of these groups are for example, methyl group, ethyl group, isopropyl group, tert-butyl group, cyclopentyl group, cyclohexyl group, vinyl group, allyl group, phenyl group, naphthyl group, tolyl group, dimethylphenyl group, benzyl group, phenylethyl group, trimethylsilyl group, trimethylgermyl group, furyl group, thienyl group, pyridyl group.

Any adjacent substituents on the cyclopentadienyl ring or rings may form a cyclic structure having 5–8 carbon atoms and the cyclic structure may be an aromatic ring. In case R1 and R2 are fused together to form an aromatic group as a cyclic structure having 6 carbon atoms, for example, it will become an indenyl ligand. The cyclic structure may have a substituent or substituents.

On synthesis of a μ-oxo-metallocene complex compound, the starting complex wherein R3 and R6 are hydrogen is easily convertible into the μ-oxo-complex and so is preferable.

The substituents R9 and R10 in a bridging portion may form a cyclic structure having 4–8 carbon atoms wherein silicon, germanium, oxygen, sulfur and nitrogen may be contained. For example, silacyclobutane and silacyclopentane can be mentioned. Noteworthy is that all of R1–R8 should not be hydrogen.

Synthesis of the μ-oxo-bis-metallocene complex compound can be carried out according to a conventional method and can be shown by the formula (3):

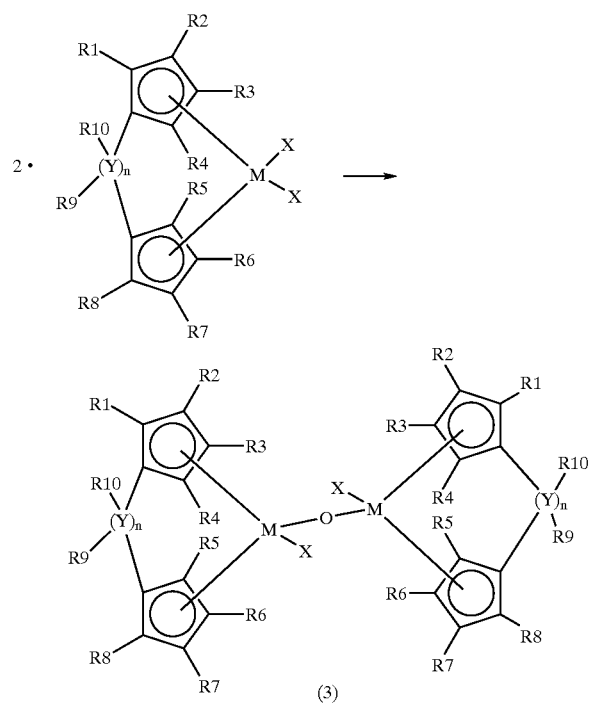

A relevant metallocene complex compound can be reacted with water to obtain the corresponding μ-oxo-bis-metallocene complex compound.

A metallocene complex compound as the starting material can be prepared, for example, according to the following process: A substituted cycloalkadiene having substituents R1–R4 is anionized by the reaction with a metal salt type base to form a substituted cycloalkadiene anion which is then reacted at a molar ratio of 1:1 with a substituted cycloalkadiene compound connected through (Y)$_n$ to (Y)$_n$—(X$^1$)$_2$ wherein X$^1$ stands for a hydrogen atom or a halogen atom, to form a compound wherein two cycloalkadienes are connected each other through Y. The latter compound is then reacted with a metal salt type base to form a dianion wherein each, of the cycloalkadiene ring is anionized. The dianion is then reacted with a transition metal compound (X)$_2$—M—(X$^2$)$_2$ wherein X$^2$ stands for a hydrogen atom or a halogen atom to obtain the metallocene complex compound.

In case the substituent X on the central metal M of a metallocene complex compound is halogen, the compound is reacted with water in the presence of a base to form a μ-oxo-bis-metallocene complex compound precipitated as salt.

No limitation exists in the amount of water to be reacted with a metallocene complex compound but 0.01–10, preferably 0.3–1.2 equiamount of water is used. In case reagents and solvents are used without any dehydrating treatment or in case the reaction is carried out in the air or in an atmosphere into which the air may be introduced, it is necessary to consider the amount of water or moisture existent in the air, reagents and solvents. If the reaction is carried out with a small amount of a metallocene complex compound, the reaction may proceed with water present in the air, reagents or solvents so that it is sometimes unnecessary to add water. In order to check how the reaction is proceeding, $^1$H-NRM measurement can be used to confirm the proceeding of the reaction by a peak ratio of a metallocene complex compound used as staring material to a μ-oxo-bis-metallocene complex compound, A temperature for the reaction is such that the metallocene complex used is not decomposed. Thus, the temperature is preferably within the range of −80° C. to 80° C. No limitation exists in the reaction solvent so far as the metallocene complex used is not decomposed. Examples of the solvent include chloroform, dichloromethane, hexane, toluene, diethyl ether, tetrahydrofuran (THF), etc.

In the event X is a halogen, the presence of a base becomes necessary. No limitation exists regarding the base, but utilizable base is inorganic basic compounds such as lithium hydroxide, sodium hydroxide, and potassium hydroxide and amines represented by the formula (4):

$$R_pNH_{3-p} \tag{4}$$

wherein p stands for an integer of 0–3, R is an alkyl group having 1–20 carbon atoms, a cycloalkyl group having 3*–20 carbon atoms, an alkenyl group with 2–20 carbon atoms, an aryl group having 6–20 carbon atoms, an alkylaryl group having 7–20 carbon atoms, or an aralkyl group having 7–20 carbon atoms, when p stands for 2 or 3, R's may be the same or different and may be combined together to form a cyclic structure having 5–8 carbon atoms which may contain silicon, oxygen, sulfur and nitrogen.

Illustrative of the amine are, for example, ammonia, ethylamine, diethylamine, triethylamine, aniline, pyrrolidine, pyridine, and tetramethylethylene diamine. In case a strong basic substance is used, there is a possibility of decomposition in a metallocene complex compound used. Accordingly, the use of a weak base such as an amine is preferable.

No special limitation exists in the amount of the basic substance used but 0.01–10 equiamount, preferably 0.8–1.2 equiamount of the basic substance is used for a metallocene complex compound.

Organometallic compounds, alkoxides, hydrides and amides of lithium, sodium, potassium, and magnesium, etc. which react with water to form water may also be used. These compounds may react, when added under anhydrous conditions, with a metallocene complex compound to replace X with a substituent on a metal reagent. In case the amount to be added is in at least 1 equiamount to the metallocene complex compound, the substituent X in a μ-oxo-bis-metallocene complex compound formed thereafter by addition of water will be replaced with a substituent of the metal At reagent. In case a μ-oxo-bis-metallocene complex compound wherein X stands for a halogen atom is to be synthesized, the metal reagent is to be added to the reaction system in the presence of water.

The purification of a bridged type metallocene complex compound is usually carried out by washing, extraction with a solvent or recrystallization. However, a large amount of a metallocene complex compound remains in residue after purification such as washing liquid and mother liquid of recrystallization and may not be recovered. By converting metallocene complex compounds into the μ-oxo-bis-metallocene complex compounds, the latter compounds could easily be recovered and separated since the μ-oxo-bis-metallocene complex compounds are excellent in crystallinity. These μ-oxo-bis-metallocene complex compounds can nevertheless be used preferentially as an essentially component for the polymerization catalyst for olefins.

In bridged-type metallocene compounds, stereoisomers may exist according to the position of substituents at the time of synthsizing the complex compounds. In order to obtain the isomer of high purity, a separation operation such as recrystallization has to be carried out repeatedly. In case an isomeric mixture is reacted with water alone or in the, presence of a basic compound, a μ-oxo-bis-metallocene complex compound consisting of a specific isomer can preferentially be formed. As a μ-oxo-bis-metallocene complex compound is excellent in crystallinity, the isomeric mixture can be brought to a separation operation such as extraction to obtain the μ-oxo-metallocene complex compound alone easily. A reaction condition in this case is such that the amount of water, absence or presence of a basic compound and the amount of the basic compound, if any, are used for the metallocene complex compound preferentially reacted, In case of an isomeric mixture consisting of the racemic form and the meso form, the meso form is preferentially converted into the μ-oxo-bis-metallocene complex compound so that the μ-oxo-bis-metallocene complex compound wherein the 2 ligands are arranged in the meso form can be separated easily by extraction or the like.

The difference between the meso form and the racemic form depend on the configuration of substituents on the ligands as shown in the following formula (5):

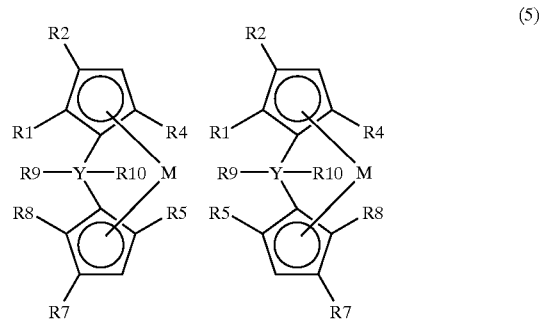

wherein R2 and R7 each stands for a substituent other than hydrogen.

Illustrative of the metallocene complex compound represented by the formula (1) wherein M stands for zirconium or hafnium, Y stands for silicon or germanium and X stands for chlorine are, for example, μ-oxo-bis[dimethylsilylene-bis(3-methylcyclopentadienyl)zirconium chloride], μ-oxo-bis [dimethylsilylene-bis(2,4-dimethylcyclopentadienyl) zirconium chloride], μ-oxo-bis[imethylsilylene-bis(2,3,5-trimethylcyclopentadienyl)zirconium chloride); μ-oxo-bis [dimethylsilylene-bis(3-tert-butylcyclopentadienyl) zirconium chloride], μ-oxo-bis[dimethylsilylene-bis(4-tert-butyl-2-methylcyclopentadienyl)zirconium chloride], μ-oxo-bis[]dimethylsilylene-bis-(3-tert-butyl-2,5-dimethylcyclopentadienyl)zirconium chloride); μ-oxo-bis [dimethylsilylene-bis(3-phenylcyclopentadienyl)zirconium chloride], μ-oxo-bis[dimethylsilylene-bis(4-phenyl-2-methylcyclopentadienyl)zirconium chloride], μ-oxo-bis-[dimethylsilylene-bis(3-phenyl-2,5-dimethylcyclopentadienyl)zirconium chloride]; μ-oxo-bis [dimethylgermylene-bis(3-methylcyclopentadienyl) zirconium chloride], μ-oxo-bis[dimethylgermylene-bis(2,4-dimethylcyclopentadienyl)zirconium chloride], μ-oxo-bis [dimethylgermylene-bis(2,3,5-trimethylcyclopentadienyl) zirconium chloride]; μ-oxo-bis[dimethylgermylene-bis(3-tert-butylcyclopentadienyl)zirconium chloride], μ-oxo-bis [dimethylgermylene-bis(4-tert-butyl-2-methylcyclopentadienyl)zirconium chloride], μ-oxo-bis [dimethylgermylene-bis(3-tert-butyl-2,5-dimethylcyclopentadienyl)zirconium chloride]; μ-oxo-bis [dimethylgermylene-bis(3-phenylcyclopentadienyl) zirconium chloride], μ-oxo-bis[dimethylgermylene-bis(4-phenyl-2-methylcyclopentadienyl)zirconium chloride], μ-oxo-bis[dimethylgermylene-bis(3-phenyl-2,5-dimethylcyclopentadienyl)zirconium chloride], μ-oxo-bis[dimethylsilylene-bis(3-methylcyclopentadienyl)hafnium chloride], μ-oxo-bis[dimethylsilylene-bis(2,4-dimethylcyclopentadienyl)hafnium chloride], μ-oxo-bis[dimethylsilylene-bis(2,3,5-trimethylcyclopentadienyl)hafnium chloride]; μ-oxo-bis[dimethylsilylene-bis(3-tert-butylcyclopentadienyl)hafnium chloride], μ-oxo-bis[dimethylsilylene-bis(4-tert-butyl-2-methylcyclopentadienyl)hafnium chloride], μ-oxo-bis[dimethylsilylene-bis(3-tert-butyl-2,5-dimethylcyclopentadienyl)hafnium chloride]; μ-oxo-bis[dimethylsilylene-bis( 3-phenylcyclopentadienyl)hafnium chloride], μ-oxo-bis[dimethylsilylene-bis-(4-phenyl-2-methylcyclopentadienyl)hafnium chloride], μ-oxo-bis[dimethylsilylene-bis(3-phenyl-2,5-dimethylcyclopentadienyl)hafnium chloride]; μ-oxo-bis[dimethylgermylene-bis(3-methylcyclopentadienyl)hafnium chloride], μ-oxo-bis[dimethylgermylene-bis(2,4-dimethylcyclopentadienyl)hafnium chloride], μ-oxo-bis[dimethylgermylene-bis(2,3,5-trimethylcyclopentadienyl)hafnium chloride]; μ-oxo-bis[dimethylgermylene-bis(3-tert-butylcyclopentadienyl)hafnium chloride], μ-oxo-bis[dimethylgermylene-bis(4-tert-butyl-2-methylcyclopentadienyl)hafnium chloride], μ-oxo-bis[dimethylgermylene-bis(3-tert-butyl-2,5-dimethylcyclopentadienyl)hafnium chloride]; μ-oxo-bis[dimethylgermylene-bis(3-phenylcyclopentadienyl)hafnium chloride], μ-oxo-bis[dimethylgermylene-bis(4-phenyl-2-methylcyclopentadienyl)hafnium chloride], μ-oxo-bis[dimethylgermylene-bis(3-phenyl-2,5-dimethylcyclopentadienyl)hafnium chloride]; μ-oxo-bis[silacyclopentane-bis(3-methylcyclopentadienyl)zirconium chloride], μ-oxo-bis[silacyclopentane-bis(2,4-dimethylcyclopentadienyl)zirconium chloride], μ-oxo-bis[silacyclopentane-bis(2,3,5-trimethylcyclopentadieny)zirconium chloride]; μ-oxo-bis[silacyclopentane-bis(3-tert-butyllcyclopentadienyl)zirconium chloride) μ-oxo-bis[silacyclopentane-bis(4-tert-butyl-2-methylcyclopentadienyl)zirconium chloride], μ-oxo-bis[silacyclopentane-bis(3-tert-butyl-2,5-dimethylcyclopentadienyl)zirconium chloride]; μ-oxo-bis[silacyclopentane-bis(3-phenylcyclopentadienyl)zirconium chloride], μ-oxo-bis[silacyclopentane-bis(4-phenyl-2-methylcyclopentadienyl)zirconium chloride], μ-oxo-bis[silacyclopentane-bis(3-phenyl-2,5-dimethylcyclopentadienyl)zirconium chloride]; μ-oxo-bis[silacyclopentane-bis(3-methylcyclopentadienyl)hafnium chloride], μ-oxo-bis(silacyclopentane-bis(2,4-dimethylcyclopentadienyl)hafnium chloride], μ-oxo-bis[silacyclopentane-bis-(2,3,5-trimethylcyclopentadienyl)hafnium chloride]; μ-oxo-bis[silacyclopentane-bis-(3-tert-butylcyclopentadienyl)hafnium chloride], μ-oxo-bis[silacyclopentane-bis(4-tert-butyl-2-methylcyclopentadienyl)hafnium chloride], μ-oxo-bis[silacyclopentane-bis(3-tert-butyl-2,5-dimethylcyclopentadienyl)hafnium chloride]; μ-oxo-bis[silacyclopentane-bis( 3-phenylcyclopentadienyl)hafnium chloride], μ-oxo-bis[silacyclopentane-bis(4-phenyl-2-methylcyclopentadienyl)hafnium chloride], μ-oxo-bis[silacyclopentane-bis(3-phenyl-2,5-dimethylcyclopentadienyl)hafnium chloride]; μ-oxo-bis[silacyclobutane-bis(2,4-dimethylcyclopentadienyl)zirconium chloride], μ-oxo-bis[silacyclobutane-bis(2,3,5-trimethylcyclopentadienyl)zirconium chloride]; μ-oxo-bis[silacyclobutane-bis(3-tert-butylcyclopentadienyl)zirconium chloride], μ-oxo-bis[silacyclobutane-bis(4-tert-butyl-2-methylcyclopentadienyl)zirconium chloride], μ-oxo-bis[silacyclobutane-bis(3-tert-butyl-2,4-dimethylcyclopentadienyl)zirconium chloride]; μ-oxo-bis[silacyclobutane-bis(3-phenylcyclopentadienyl)zirconium chloride], μ-oxo-bis[silacyclobutane-bis(4-phenyl-2-methylcyclopentadienyl)zirconium chloride], μ-oxo-bis[silacyclobutane-bis(3-phenyl-2,5-dimethylcyclopentadienyl)zirconium chloride]; μ-oxo-bis[silacyclobutane-bis(3-methylcyclopentadienyl)-hafnium chloride], μ-oxo-bis[silacyclobutane-bis(2,4-dimethylcyclopentadienyl)hafnium chloride]μ-oxo-bis[silacyclobutane-bis(2,4-dimethylcyclopentadienyl)hafnium chloride], μ-oxo-bis[silacyclobutane-bis(2,3,5-trimethylcyclopentadienyl)hafnium chloride]; μ-oxo-bis[silacyclobutane-bis(3-tert-butylcyclopentadienyl)hafnium chloride], μ-oxo-bis[silacyclobutane-bis(4-tert-butyl-2-methylcyclopentadienyl)hafnium chloride], μ-oxo-bis[silacyclobutane-bis(3-tert-butyl-2,5-dimethylcyclopentadienyl)hafnium chloride]; μ-oxo-bis[silacyclobutane-bis(3-phenylcyclopentadienyl)hafnium chloride], μ-oxo-bis[silacyclopentane-bis(4-phenyl-2-methylcyclopentadienyl)hafnium chloride], μ-oxo-bis[silacyclobutane-bis(3-phenyl-2,5-dimethylcyclopentadienyl)hafnium chloride]; μ-oxo-bis[dimethylsilylene-bis(tetrahydroindenyl)zirconium chloride], μ-oxo-bis[dimethylsilylene-bis(2-methyltetrahydroindenyl)zirconium chloride], μ-oxo-bis[dimethylsilylene-bis(indenyl)zirconium chloride], μ-oxo-bis[dimethylsilylene-bis(2-methylindenyl)zirconium chloride], μ-oxo-bis[dimethylsilylene-bis(2-methyl-4,5-benzoindenyl)zirconium chloride], μ-oxo-bis[dimethylsilylene-bis(2-methyl-4-phenylindenyl)zirconium chloride], μ-oxo-bis[dimethylsilylene-bis(2-methyl-4-naphthylindenyl)zirconium chloride], μ-oxo-bis[dimethylsilylene-bis( 1-cyclopentaphenanthryl)zirconium chloride], μ-oxo-bis[dimethylsilylene-bis-[1-(2-methylcyclopenta)phenanthryl)zirconium chloride], μ-oxo-bis-[dimethylsilylene-bis [1-(2-methylcyclopenta)phenanthryl)zirconium chloride]; μ-oxo-bis[dimethylgermylene-bis(tetrahydroindenyl)zirconium chloride], μ-oxo-bis-[dimethylgermylene-bis(2-methyltetrahydroindenyl)zirconium chloride], μ-oxo-bis-[dimethylgermylene-bis (indenyl)zirconium chloride], μ-oxo-bis[dimethylgermylene-bis(2-methylindenyl)zirconium chloride], μ-oxo-bis[dimethylgermylene-bis(2-methyl-4,5-benzoindenyl)zirconium chloride], μ-oxo-bis[dimethylgermylene-bis(2-methyl-4-phenylindenyl)zirconium chloride], μ-oxo-bis[dimethylgermylene-bis(2-methyl-4-naphthylindenyl)zirconium chloride], μ-oxo-bis[dimethylgermylene-bis(1-cyclopentaphenanthryl)zirconium chloride], μ-oxo-bis[dimethylgermylene-bis[1-(2-methylcyclopenta)phenanthryl]zirconium chloride]; μ-oxo-bis[dimethylsilylene-bis(tetrahydroindenyl) hafnium chloride], μ-oxo-bis(dimethylsilylene-bis(2-methyltetrahydroindenyl) hafnium chloride], μ-oxo-bis[dimethylsilylene-bis(indenyl)hafnium chloride], μ-oxo-bis[dimethylsilylene-bis(2-methylindenyl)hafnium chloride], μ-oxo-bis[dimethylsilylene-bis(2-methyl-4,5-benzoindenyl) hafnium chloride], μ-oxo-bis[dimethylsilylene-bis (2methyl4-phenylindenyl)hafnium chloride], μ-oxo-bis-[dimethylsilylene-bis(2-methyl-4-naphthylindenyl)hafnium chloride], μ-oxo-bis-[dimethylsilylene-bis(1-cyclopentaphenanthryl)hafnium chloride], μ-oxo-bis[dimethylsilylene-bis(1-(2-methylcyclopenta)phenanthryl) hafnium chloride]; μ-oxo-bis-[dimethylgermylene-bis(tetrahydroindenyl)hafnium chloride], μ-oxo-bis(dimethylgermylene-bis(2-methyltetrahydroindenyl)

hafnium chloride], μ-oxo-bis[dimethylgermylene-bis(indenyl)hafnium chloride], μ-oxo-bis[dimethylgermylene-bis(2-methylindenyl)hafnium chloride], μ-oxo- bis[dimethylgermylene-bis(2-methyl-4,5-benzoindenyl)hafnium chloride], μ-oxo-bis[dimethylgermylene-bis(2-methyl-4-naphthylindenyl)hafnium chloride], μ-oxo-bis[dimethylgermylene-bis(1-cyclopentaphenanthryl)hafnium chloride], μ-oxo-bis[dimethylgermylene-bis(1-(2-methylcyclopenta)phenanthryl)hafnium chloride]; μ-oxo-bis[dimethylsilylene(cyclopentadienyl)-( 2,3,5-trimethylcyclopentadienyl)zirconium chloride], μ-oxo-bis[dimethylsilylene(3-methylcyclopentadienyl)(2,3,5-trimethylcyclopentadienyl)zirconium chloride], μ-oxo-bis[dimethylsilylene(2,4-dimethylcyclopentadieny)(2,3,5-trimethylcyclopentadienyl)-zirconium chloride], μ-oxo-bis[dimethylsilylene(3-tert-butylcyclopentadienyl)(2,3,5-trimethylcyclopentadienyl) zirconium chloride], μ-oxo-bis[dimethylsilylene(2-methyl-4-tert-butycyclopentadieny)(2,3,5-trimethylcyclopentadienyl)zirconium chloride], μ-oxo-bis[dimethylsilylene(2,5-dimethyl-3-tert-butylcyclopentadieny)(2,3,5-trimethylcyclopentadienyl) zirconium chloride]; μ-oxo-bis[dimethylsilylene(3-phenylcyclopentadienyl)(2,3,5-trimethylcyclopentadienyl) zirconium chloride], μ-oxo-bis-[dimethylsilylene(2-methyl-4-phenylcyclopentadieny)(2,3,5-trimethylcyclopentadienyl) zirconium chloride], μ-oxo-bis[dimethylsilylene(2,5-dimethyl-3-phenylcyclopentadieny)(2,3,5-trimethylcyclopentadienyl)zirconium chloride]; μ-oxo-bis[dimethylsilylene (cyclopentadienyl)(2,4-dimethylcyclopentadienyl)zirconium chloride], μ-oxo-bis[dimethylsilylene(3-methylcyclopentadienyl)(2,4-dimethylcyclopentadienyl)zirconium chloride], μ-oxo-bis[dimethylsilylene(3-tert-butylcyclopentadienyl)(2,4-dimethylcyclopentadienyl)zirconium chloride], μ-oxo-bis[dimethylsilylene(2-methyl-4-tert-butylcyclopentadienyl)(2,4-dimethylcyclopentadienyl)zirconium chloride], μ-oxo-bis[dimethylsilylene(2,5-dimethyl-4-tert-butylcyclopentadienyl)(2,4-dimethylcyclopentadienyl) zirconium chloride], μ-oxo-bis[dimethylsilylene(2-methyl-4-phenylcyclopentadienyl) (2,4-dimethylcyclopentadienyl) zirconium chloride], μ-oxo-bis[dimethylsilylene(2,5-dimethyl-3-phenylcyclopentadienyl)(2, 4-dimethylcyclopentadienyl)-zirconium chloride]; μ-oxo-bis[dimethylsilylene(cyclopentadienyl)(3-methylcyclopentadienyl) zirconium chloride]; μ-oxo-bis[dimethylsilylene(3-methylcyclopentadienyl)(3-tert-butylcyclopentadienyl)zirconium chloride], μ-oxo-bis[dimethylsilylene(3-methylcyclopentadienyl)(2-methyl-4-tert-butylcyclopentadienyl)zirconium chloride], μ-oxo-bis[dimethylsilylene(3-methylcyclopentadienyl)(2,5-dimethyl-3-tert-butylcyclopentadienyl)zirconium chloride], μ-oxo-bis[dimethylsilylene(3-methylcyclopentadienyl)(3-phenylcyclopentadienyl)zirconium chloride], μ-oxo-bis[dimethylsilylene(3-methylcyclopentadienyl)(2-methyl-4-phenylcyclopentadienyl)zirconium chloride], μ-oxo-bis[dimethylsilylene(3-methylcyclopentadienyl)(2,5-dimethyl-3-phenylcyclopentadienyl) zirconium chloride]; μ-oxo-bis[dimethylsilylene(cyclopentadienyl)(3-tert-butylcyclopentadienyl)zirconium chloride], μ-oxo-bis[dimethylsilylene(cyclopentadienyl) (2-methyl-4-tert-butylcyclopentadienyl)zirconium chloride], μ-oxo-bis[dimethylsilylene (cyclopentadienyl)(2,5-dimethyl-3-tert-butylcyclopentadienyl)zirconium chloride], μ-oxo-bis[dimethylsilylene(cyclopentadienyl)(3-phenylcyclopentadienyl)zirconium chloride], μ-oxo-bis[dimethylsilylene(cyclopentadienyl)(2-methyl-4-phenylcyclopentadienyl)zirconium chloride], μ-oxo-bis[dimethylsilylene(cyclopentadienyl)(2,5-dimethyl-3-phenylcyclopentadienyl)zirconium chloride]; μ-oxo-bis[dimethylsilylene(cyclopentadienyl)(2-methylindenyl)zirconium chloride], μ-oxo-bis[dimethylsilylene(3-methylcyclopentadienyl)(2-methylindenyl)zirconium chloride], μ-oxo-bis[dimethylsilylene (2,4-dimethylcyclopentadienyl)(2-methylindenyl)zirconium chloride], μ-oxo-bis[dimethylsilylene(2,3,5-triimethylcyclopentadienyl)(2-methylindenyl) zirconium chloride], μ-oxo-bis[dimethylsilylene(3-tert-butylclopentadienyl)-(2-methylindenyl)zirconium chloride], μ-oxo-bis[dimethylsilylene(2-methyl-4-tert-butylcyclopentadienyl)(2-methylindenyl)zirconium chloride], μ-oxo-bis[dimethylsilylene(3-phenylcyclopentadienyl)(2-methylindenyl)zirconium chloride], μ-oxo-bis[dimethylsilylene(3-phenyl-2,5-dimethylcyclopentadienyl)(2-methylindenyl)zirconium chloride]; μ-oxo-bis[ethylene-bis(3-methylcyclopentadienyl)zirconium chloride], μ-oxo-bis[ethylene-bis(2,4-dimethylcyclopentadienyl)zirconium chloride], μ-oxo-bis[ethylene-bis(2,3,5-triimethylcyclopentadienyl)zirconium chloride], μ-oxo-bis[ethylene-bis(4-tert-butyl-2-methylcyclopentadienyl) zirconium chloride], μ-oxo-bis[ethylene-bis(3-tert-butyl-2,5-dimethylcyclopentadienyl)zirconium chloride], μ-oxo-bis[ethylene-bis(3-phenylcyclopentadienyl)zirconium chloride], μ-oxo-bis-[ethylene-bis(4-phenyl-2-methylcyclopentadienyl)zirconium chloride], μ-oxo-bis-[ethylene-bis(3-phenyl-2,5-dimethylcyclopentadienyl) zirconium chloride], μ-oxo-bis[ethylene-bis(tetrahydroindenyl)zirconium chloride]; μ-oxo-bis[ethylene-bis( 2-methylindenyl)zirconium chloride], μ-oxo-bis[ethylene-bis(2-methyl-4,5-benzoindenyl)zirconium chloride], μ-oxo-bis[ethylene-bis(2-methyl-4-phenylindenyl)-zirconium chloride], μ-oxo-bis[ethylene-bis(2-methyl-4-naphthylindenyl)zirconium chloride], μ-oxo-bis[ethylene-bis(1-cyclopentaphenanthryl)zirconium chloride], μ-oxo-bis[ethylene-bis[1-(2-methylcyclopenta) phenanthryl]zirconium chloride]; μ-oxo-bis[ethylene-bis(3-methylcyclopentadienyl)hafnium chloride], μ-oxo-bis[ethylene-bis(2,4-dimethylcyclopentadienyl)hafnium chloride], μ-oxo-bis[ethylene-bis(2,3,5-trimethylcyclopentadienyl)hafnium chloride]; μ-oxo-bis[ethylene-bis(3-tert-butylcyclopentadienyl)hafnium chloride], μ-oxo-bis[ethylene-bis(4-tert-butyl-2-methylcyclopentadienyl)hafnium chloride], μ-oxo-bis[ethylene-bis(3-tert-butyl-2,5-dimethylcyclopentadienyl) hafnium chloride]; μ-oxo-bis[ethylene-bis(3-phenylcyclopentadienyl)hafnium chloride], μ-oxo-bis[ethylene-bis(4-phenyl-2-methylcyclopentadienyl)hafnium chloride]; μ-oxo-bis[ethylene-bis(3-phenyl-2,5-dimethylcyclopentadienyl)hafnium chloride]; μ-oxo-bis[ethylene-bis(tetrahydroindenyl)hafnium chloride], μ-oxo-bis[ethylene-bis(indenyl)hafnium chloride], μ-oxo-bis[ethylene-bis(2-methylindenyl)hafnium chloride], μ-oxo-bis[ethylene-bis(2-methyl-4,5-benzoindenyl)hafnium chloride], μ-oxo-bis[ethylene-bis(2-methyl-4-phenylindenyl)hafnium chloride], μ-oxo-bis[ethylene-bis(2-methyl-4-naphthylindenyl)hafnium chloride], μ-oxo-bis[ethylene-bis(1-cyclopentaphenanthryl)hafnium chloride], μ-oxo-bis(ethylene-bis[1-(2-methylcyclopenta)phenanthryl]hafnium chloride]; μ-oxo-bis[dimethylsilylene-bis(3-tolylcyclopentadienyl)zirconium chloride], μ-oxo-bis[dimethylsilylene-bis(4-tolyl-2-methylcyclopentadienyl) zirconium chloride], μ-oxo-bis-[dimethylsilylene-bis(3-tolyl-2,5dimethylcyclopentadienyl)zirconium chloride]; μ-oxo-bis[dimethylsilylene-bis(3- ethylphenylcyclopentadienyl)zirconium chloride], μ-oxo-bis[dimethylsilylene-bis(4-ethylphenyl-2-methylcyclopentadienyl)zirconium chloride], μ-oxo-bis[dimethylsilylene-bis(3-ethylphenyl-2,5-dimethylcyclopentadienyl)-zirconium chloride]; μ-oxo-bis[dimethylsilylene-bis(3-fluorophenylcyclopentadienyl)zirconium chloride], μ-oxo-bis[dimethylsilylene-bis(4-fluorophenyl- 2-methyl-cyclopentadienyl)zirconium chloride], μ-oxo-bis[dimethylsilylene-bis(3-fluorophenyl-2,5-dimethylcyclopentadienyl)zirconium chloride]; μ-oxo-bis[dimethylsilylene-bis(3-naphthylcyclopentadienyl)zirconium chloride], μ-oxo-bis[dimethylsilyienebis(4-naphthyl-2-methylcyclopentadienyl)zirconium chloride], μ-oxo-bis(dimethylsilylene-bis(3-naphthyl-2,5-dimethylcyclopentadienyl)zirconium chloride]; μ-oxo-bis[dimethylgermylene-bis(3-tolylcyclopentadienyl)zirconium chloride], μ-oxo-bis [dimethylgermylene-bis(4-tolyl-2-methylcyclopentadienyl)zirconium chloride], μ-oxo-bis[dimethylgermylene-bis(3-tolyl-2,5-dimethylcyclopentadienyl)zirconium chloride]; μ-oxo-bis[dimethylgermylene-bis(3-ethylphenylcyclopentadienyl)zirconium chloride], μ-oxo-bis[dimethylgermylene-bis(4-ethylphenyl-2-(methylcylopentadienyl)zirconium chloride], μ-oxo-bis[dimethylgermylene-bis(3-ethylphenyl-2,5-dimethylcyclopentadienyl)zirconium chloride]; μ-oxo-bis[dimethylgermylene-bis(3-fluorophenylcyclopentadienyl)zirconium chloride], μ-oxo-bis[dimethylgermylene-bis(4-fluorophenyl-2-methylcyclopentadienyl)zirconium chloride], μ-oxo -bis[dimethylgermylene-bis(3-fluorophenyl-2,5-dimethylcyclopentadienyl)zirconium chloride]; μ-oxo-bis [dimethylgermylene-bis(3-naphthylcyclopentadienyl)zirconium chloride], μ-oxo-bis[dimethylgermylene-bis(4-naphthyl-2-methylcyclopentadienyi)zirconium chloride], μ-oxo-bis[dimethylgermylene-bis(3-naphthyl-2,5-dimethylcyclopentadienyl)zirconium chloride]; μ-oxo-bis[dimethylsilylene-bis(3-tolylcyclopentadienyl)hafnium chloride], μ-oxo-bis[dimethylsilylene-bis(4-tolyl-2-methylcyclopentadienyl)hafnium chlorode], dimethylsilylene-bis(3-tolyl-2,5-dimethylcyclopentadienyl)hafnium chloride]; μ-oxo-bis[dimethylsilylene-bis(3-ethylphenylcyclopentadienyl)hafnium chloride], μ-oxo-bis[dimethylsilylene-bis(4-ethylphenyl-2-methylcyclopentadienyl)hafnium chloride], μ-oxo-bis[dinethylsilylene-bis(3-ethylphenyl-2,5-dimethylcyclopentadienyl)hafnium chloride]; μ-oxo-bis[dimethylsilylene-bis(3-fluorophenylcyclopentadienyl)hafnium chloride], μ-oxo-bis[dimethylsilylene-bis(4-fluorophenyl-2-methylcyclopentadienyl)hafnium chloride], μ-oxo-bis[dimethylsilylene-bis(3-fluorophenyl-2,5-dimethylcyclopentadienyl)hafnium chloride]; μ-oxo-bis[dimethylsilylene-bis( 3-naphthylcyclopentadienyl)hafnium chloride], μ-oxo-bis[dimethylsilylene-bis(4-naphthyl-2-methylcyclopentadienyl)hafnium chloride], μ-oxo-bis[dimethylsilylene-bis(3-naphthyl-2,5-dimethylcyclopentadienyl)hafnium chloride]; μ-oxo-bis[dimethylgermylene-bis(3-tolylcyclopentadienyl)hafnium chloride], μ-oxo-bis[dimethylgermylene-bis(4-tolyl-2-methylcyclopentadienyl)hafnium chloride], μ-oxo-bis[dimethylgermylene-bis(3-tolyl-2,5-dimethylcyclopentadienyl)hafnium chloride], μ-oxo-bis[dimethylgermylene-bis(3-ethylphenylcyclopentadienyl)hafnium chloride], μ-oxo-bis[dimethylgermylene-bis(4-ethylphenyl-2-methylcyclopentadienyl)hafnium chloride], μ-oxo-bis [dimethylgermylene-bis(3-ethylphenyl-2,5-dimethylcyclopentadienyl)hafnium chloride]; μ-oxo-bis[dimethylgermylene-bis(3-fluorophenylcyclopentadienyl) hafnium chloride], μ-oxo-bis[dimethylgermylene-bis(4-fluorophenyl-2-methylcyclopentadienyl)hafnium chloride], μ-oxo-bis[dimethylgermylene-bis(3-fluorophenyl-2,5-dimethylcyclopentadienyl)hafnium chloride]; μ-oxo-bis[dimethylgermylene-bis(3-naphthylcyclopentadienyl)hafnium chloride], μ-oxo-bis[dimethylgermylene-bis(4-naphthyl-2-methyl-cyclopentadienyl)hafnium chloride], μ-oxo-bis[diiethylgermylene-bis(3-naphthyl-2,5-dimethylcyclopentadienyl)hafnium chloride]; μ-oxo-bis[silacyclobutane-bis(3-tolylcyclopentadienylzirconium chloride], μ-oxo-bis[silacyclobutane-bis(4-tolyl-2-methylcyclopentadienyl)zirconium chloride], μ-oxo-bis[silacylobutane-bis(3-tolyl-2,5-dimethylcyclopentadienyl)zirconium chloride]; μ-oxo-bis[silacyclobutane-bis(3-ethylphenylcyclopentadienyl)zirconium chloride], μ-oxobis[silacyclobutane-bis(4-ethylphenyl-2-methylcyclopentadienyl)zirconium chloride], μ-oxo-bis[silacyclobutane-bis(3-ethylphenl-2,5-dimethylcyclopentadienyl)zirconium chloride]; μ-oxo-bis[silacyclobutane-bis(3-fluorophenycyclopentadienyl)zirconium chloride], μ-oxo-butane-bis(4-fluorphenyl-2dethylcyclopentadienyl)zirconium chloride], μ-oxo-bis[silacyclobutane-bis(3-fluorophenyl-2,5-dimethylcyclopentadienyl)zirconium chloride]; μ-oxo-bis[silacyclobutane-bis(3-naphthylcyclopentadienyl)zirconium chloride], μ-oxo-bis[silacyclobutane-bis(4-naphthyl-2-methylcyclopentadienyl)zirconium chloride], μ-oxo-bis[silacyclobutane-bis(3-naphthyl-2,5-dimethylcyclopentadienyl)zirconium chloride]; μ-oxo-bis[silacyclobutane-bis(3-tolylcyclopentadienyl)hafnium chloride], μ-oxo-bis[silacyclobutane-bis(4-tolyl-2-methylcyclopentadienyl)hafnium chloride], μ-oxo-bis[silacyclobutane-bis(3-tolyl-2,5-dimethylcyclopentadienyl)hafnium chloride]; μ-oxo-bis[silacyclobutane-bis(3-ethylphenylcyclopentadienyl)hafnium chloride], μ-oxo-bis[silacyclobutane-bis(4-ethylphenyl-2-methylcyclopentadienyl)hafnium chloride], μ-oxo-bis[silacyclobutane-bis(3-ethylphenyl-2,5-dimethylcyclopentadienyl)hafnium chloride]; μ-oxo-bis[silacyclobutane-bis(3-fluorophenylcyclopentadienyl)hafnium chloride], μ-oxo-bis[silacyclobutane-bis(4-fluorophenyl-2-methylcyclopentadienyl)hafnium chloride], μ-oxo-bis[silacyclobutane-bis(3-fluorophenyl-2,5-dimethylcyclopentadienyl)hafnium chloride]; μ-oxo-bis[silacyclobutane-bis(3-naphthylcyclopentadienyl)hafnium chloride], μ-oxo-bis[silacyclobutane-bis(4-naphthyl-2-methylcyclopentadienyl)hafnium chloride], μ-oxo-bis[silacyclobutane-bis-(3-naphthyl-2,5-dimethylcyclopentadienyl)hafnium chloride]; μ-oxo -bis[silacyclopentane-bis(3-tolylcyclopentadienyl)zirconium chloride], μ-oxo-bis[silacyclopentane-bis(4-tolyl-2-methylcyclopentadienyl)zirconium chloride], μoxo-bis[silacyclopentane-bis(3-tolyl-2,5-dimethylcyclopentadienyl)zirconium chloride]; μ-oxo-bis-[silacyclopentane-bis(3-ethylphenylcyclopentadienyl)zirconium chloride], μ-oxo-bis-[silacyclopentane-bis(4-ethylphenyl-2-methycyclopentadienyl)zirconium chloride], μ-oxo-bis[silacyclopentane-bis(3-ethylphenyl -2,5-dimethylcyclopentadienyl)zirconium chloride]; μ-oxo-bis[silacyclopentane-bis(3-fluorophenylcyclopentadienyl)zirconium chloride], μ-oxo-bis[silacyclopentane-bis(4-fluorophenyl-2-methylcyclopentadienyl)ziconium chloride], μ-oxo-bis[silacyclopentane-bis(3-fluorophenyl-2,5-dimethylcyclopentadienyl)zirconium chloride]; μ-oxo-bis[silacyclopentane-bis(3-naphthylcyclopentadienyl)zirconium chloride], μ-oxo-bis[silacyclopentane-bis(4-naphthyl-2-methylcyclopentadienyl)zirconium chloride], μ-oxo-bis[silacyclopentane-bis(3-naphthyl-2,5-dimethylcyclopentadienyl)zirconium chloride]; μ-oxo-bis[silacyclopentane-bis(3-tolylcyclopentadienyl)hafnium chloride], μ-oxo-bis[silacyclopentane-bis(4-tolyl-2-methylcyclopentadienyl)hafnium chloride], μ-oxo-bis[silacyclopentane-bis(3-tolyl-2,5-dimethylcyclopentadienyl)zirconium chloride]; μ-oxo-bis[silacyclopentane-bis(3-ethylphenylcyclopentadienyl)hafnium chloride], μ-oxo-bis[silacyclopentane-bis(4-ethylphenyl-2-methylcyclopentadienyl)hafnium chloride], μ-oxo-bis-[silacyclopentane-bis(3-ethylphenyl-2,5-dimethylcyclopentadienyl)zirconium chloride; μ-oxo-bis[silacyclopentane-bis(3-fluorophenylcyclopentadienyl)hafnium chloride], μ-oxo-bis[silacyclopentane-bis(4-fluorophenyl-2-methylcyclopentadienyl)hafnium chloride], μ-oxo-bis[silacyclopentane-bis(3-fluorophenyl-2,5-dimethylcyclopentadienyl)zirconium chloride]; μ-oxo-bis[silacyclopentane-bis(3-naphthylcyclopentadienyl)hafnium chloride], μ-oxo-bis[silacyclopentane-bis(4-naphthyl-2-methylcyclopentadienyl)hafnium chloride], μ-oxo-bis[silacyclopentane-bis(3-naphthyl-2,5-dimethylcyclopentadienyl)hafnium chloride]; μ-oxo-bis[dimethylsilylene-bis(tetrahydroindenyl]hafnium chloride], μ-oxo-bis[dimethylsilylene-bis(2-methyltetrahydroindenyl)hafnium chloride], μ-oxo-bis[dimethylsilylene-bis-(indenyl)hafnium chloride], μ-oxo-bis[dimethylsilylene-bis(2-methylindenyl)hafnium chloride], μ-oxo-bis[dimethylsilylene-bis(2-methyl-4,5-benzoindenyl)hafnium chloride], μ-oxo-bis[dimethysilylene-bis(2-methyl-4-phenylindenyl)hafnium chloride], μ-oxo-bis[ditnethylsilylene-bis(2-methyl-4-naphthylindenyl)hafnium chloride], μ-oxo-bis[dimethylsilylene-bis(1-cyclopentaphenanthryl)hafnium chloride], μ-oxo-bis[dimethylsilylene-bis[1-(2-methylcyclopenta)phenanthryl]hafnium chloride]; μ-oxo-bis[dimethylgermylene-bis (tetrahydroindenyl)hafnium chloride], μ-oxo-bis[dimethylgermylene-bis(2-methyltetrahydroindenyl)hafnium chloride], μ-oxo-bis[dimethylgermylene-bis-(indenyl)hafnium chloride], μ-oxo-bis[dimethylgermylene-bis(2-methylindenyl)hafnium chloride], μ-oxo-bis[dimethylgermylene-bis(2-methyl-4,5-benzoindenyl)hafnium chloride], μ-oxo-bis[dimethylgermylene-bis(2-methyl-4-phenylindenyl)hafnium chloride], μ-oxo-bis[dimethylgermylene-bis(2-methyl-4-naphthylindenyl)hafnium chloride], μ-oxo-bis[dimethylgermylene-bis(1-cyclopentaphenanthrylindenyl)hafnium chloride], μ-oxo-bis[dimethylgermylene-bis]1-(2-methylcyclopenta)phenanthryl]-hafnium chloride]; μ-oxo-bis[dimethylsilylene-bis( 2-methyltetrahydroindenyl)zirconium chloride], μ-oxo-bis[dimethylsilylene-bis(2-methylindenyl)zirconium chloride], μ-oxo-bis[dimethylsilylene-bis(2-methyl-4,5-benzoindenyl)zirconium chloride], μ-oxo-bis[dimethylsilylene-bis(2-methyl-4-phenylindenyl)zirconium chloride], μ-oxo-bis[dimethylsilylene-bis(2-methyl-4-naphthylindenyl)zirconium chloride], μ-oxo-bis[dimethylsilylene-bis[1-(2-methylcyclopent)phenanthryl]zirconium chloride]; μ-oxo-bis[dimethylgermylene-bis(2-methyltetrahydroindenyl)zirconium chloride], μ-oxo-bis[dimethylgermylene-bis(2-methylindenyl)zirconium chloride], μ-oxo-bis[dimethylgermylene-bis(2-methyl-4,5-benzoindenyl)zirconium chloride], μ-oxo-bis[dimethylgermylene-bis(2-methyl-4-phenylindenyl)zirconium chloride], μ-oxo-bis[dimethylgermylene-bis(2-methyl-4-naphthylindenyl)zirconium chloride], μ-oxo-bis[dimethylgermylene-bis[1-(2-methylcyclopenta)phenanthryl]zirconium chloride]; μ-oxo-bis[dimethylsilytene-bis(2-methyftetrahydroindenyl)hafnium chloride], μ-oxo-bis[dimethylsilylene-bis(2-methylindenyl)hafnium chloride], μ-oxo-bis[dimethylsilylene-bis(2-methyl-4,5-benzoindenyl)hafnium chloride], μoxo-bis[dimethylsilylene-bis(2-methyl-4-phenylindenyl)hafnium chloride], μ-oxo-bis[dimethylsilylene-bis(2-methyl-4-naphthylindenyl)hafnium chloride], μ-oxo-bis[dimethylsilylene-bis[1-(2-methylcyclopenta)phenanthryl]hafnium chloride]; μ-oxo-bis[dimethylgermylene-bis(2-methyltetrahydroindenyl)hafnium chloride], μ-oxo-bis[dimethylgermylene-bis(2-methyhlindenyl)hafnium chloride], μ-oxo-bis[dimethylgermylene-bis(2-methyl-4,5-benzoindenyl)hafnium chloride], μ-oxo-bis[dimethylgermylene-bis(2-methyl-4-phenyl indenyl)hafnium chloride], μ-oxo-bis[dimethylgermylene-bis(2-methyl-4-naphthylindenyl)hafnium chloride], μ-oxo-bis[dimethylgermylene-bis[1-(2-methylcyclopenta)phenanthryl]hafnium chloride]; μ-oxo-bis-[dimethylsilylene-bis(2-ethyltetrahydroindenyl)zirconium chloride], μ-oxo-bis[dimethylsilylene-bis(2-ethylindenyl)zirconium chloride], μ-oxo-bis[dimethylslylene-bis(2-ethyl-4,5-benzoindenyl)zirconium chloride], μ-oxo-bis[dimethylsilylene-bis(2-ethyl-4-phenylindenyl)zirconium chloride], μ-oxo-bis[dimethylsilylene-bis(2-ethyl-4-naphthylindenyl)zirconium chloride], μ-oxo-bis[dimethylsilylene-bis (1-( 2-ethyl-cyclopenta)phenanthryl]zirconium chloride]; μ-oxo-bis[dimethylgermylene-bis(2-ethyltetrahydroindenyl)zirconium chloride], μ-oxo-bis[dimethylgermylene-bis(2-ethylindenyl)zirconium chloride], μ-oxo-bis[dimethylgermylene-bis(2-ethyl-4,5-benzoindenyl)zirconium chloride], μ-oxo-bis[dimethylgermylene-bis(2-ethyl-4-phenylindenyl)zirconium chloride], μ-oxo-bis[dimethylgermylene-bis(2-ethyl-4-naphthylindenyl)zirconium chloride], μ-oxo-bis[dimethylgermylene-bis (1-(2-ethyl-cyclopenta)phenanthryl]zirconium chloride]; μ-oxo-bis[dimethylsilylene-bis(2-ethyl-tetrahydroindenyl)hafnium chloride], μ-oxo-bis[dimethylsilylene-bis(2-ethylindenyl)hafnium chloride], μ-oxo-bis (dimethylsilylene-bis(2-ethyl-4,5-benzoindenyl)hafnium chloride], μ-oxo-bis[dimethylsilylene-bis(2-ethyl-4-phenylindenyl)hafnium chloride], μ-oxo-bis[dimethylsilylene-bis(2-ethyl-4-naphthylindenyl)hafnium chloride], μ-oxo-bis[dimethylsilylene-bis[1-(2-ethylcyclopenta)phenanthryl]hafnium chloride]; μ-oxo-bis[dimethylgermylene-bis(2-ethyltetrahydroindenyl)hafnium chloride], μ-oxo-bis[dimethylgermylene-bis(2-ethylindenyl)hafnium chloride], μ-oxo-bis[dimethylgermylene-bis(2-ethyl-4,5-benzoindenyl)hafnium chloride], μ-oxo-bis[dimethylgermylene-bis(2-ethyl-4-phenylindenyl)hafnium chloride], μ-oxo-bis[dimethylgermylene-bis(2-ethyl-4-naphthylindenyl)hafnium chloride], μ-oxo-bis[dimethylgermylene-bis[1-(2-ethylcyclopenta)phenanthryl]hafnium chloride]; μ-oxo-bis[dimethysilylene-bis(2-isopropyltetrahydroindenyl)zirconium chloride], μ-oxo-bis[dimethylsilylene-bis(2-isopropylindenyl)zirconium chloride], μ-oxo-bis[dimethylsilylene-bis(2-isopropyl-4,5-benzoindenyl)zirconium chloride], μ-oxo-bis[dimethylsilylene-bis(2-isopropyl-4-phenylindenyl)zirconium chloride], μ-oxo-bis[dimethylsilylene-bis(2-isopropyl-4-naphthylindenyl)zirconium chloride], μ-oxo-bis[dimethylthylene-bis(2-isopropylcyclopenta)phenanthryl]zirconium chloride]; μ-oxo-bis[dimethylgerylene-bis(2-isopropyltetrahydroindenyl)zirconium chloride], μ-oxo-bis[dimethylgerylene-bis(2-isopropylindenyl)zirconium chloride], μ-oxo-bis[dimethylgerylene-bis(2-isopropyl-4,5-benzoindenyl)zirconium chloride], μ-oxo-bis[dimethylsilmylene-bis(2-isopropyl-4-phenylindenyl)

zirconium chloride], μ-oxo-bis[dimethylgermylene-bis(2-isopropyl-4-naphthylindenyl)zirconium chloride], μ-oxo-bis[dimethylgermylene-bis[1-(2-isopropylcyclopenta)phenanthryl]zirconium chloride]; dimethylsilylene-bis(2-isopropyltetrahydroindenyl)hafnium chloride], μ-oxo-bis[dimethylsilylene-bis(2-isopropylindenyl)hafnium chloride], μ-oxo-bis[dimethylsilylene-bis(2-isopropyl-4,5-benzoindenyl)hafnium chloride], μ-oxo-bis[dimethylsilylene-bis(2-isopropyl-4-phenylindenyl)hafnium chloride], μ-oxo-bis[dimethylsilylene-bis(2-isopropyl-4-naphthylindenyl)hafnium chloride], μ-oxo-bis[dimethylsilylene-bis[1-(2-isopropylcyclopenta)phenanthryl]hafnium chloride]; μ-oxo-bis[dimethylgermylene-bis(2-isopropyltetrahydroindenyl)hafnium chloride], μ-oxo-bis[dimethylgermylene-bis(2-isopropylindenyl)hafnium chloride], μ-oxo-bis[dimethylgermylene-bis(2-isopropyl-4,5-benzoindenyl)hafnium chloride], μ-oxo-bis[dimethylgermylene-bis(2-isopropyl-4-phenylindenyl)hafnium chloride], μ-oxo-bis[dimethylgermylene-bis(2-isopropyl-4-naphthylindenyl)hafnium chloride], μ-oxo-bis[dimethylgermylene-bis[1-(2-isopropyl cyclopenta)phenanthryl]hafnium chloride]; μ-oxo-bis[tetramethylethylene-bis(3-tert-butylcyclopentadienyl)zirconium chloride], μ-oxo-bis[tetramethylethylene-bis(4-tert-butyl-2-methylcyclopentadienyl)zirconium chloride], μ-oxo-bis(tetramethylethylene-bis[3-tertbutyt-2,5-dimethylcyclopentadienyl)zirconium chloride]; μ-oxo-bis[tetranethylethylene-bis(3-phenylcyclopentadienyl)zirconium chloride], μ-oxo-bis (tetramethylethylene-bis[4-phenyl-2-methyl-cyclopentadienyl)-zirconium chloride], μ-oxo-bis[tetramethylethylene-bis(3-phenyl-2,5-dimethylcyclopentadienyl)zirconium chloride]; μ-oxo-bis[tetramethylethylene-bis(tetrahydroindenyl)zirconium chloride], μ-oxo-bis[tetraiethylethylene-bis-(indenyl)zirconium chloride], μ-oxo-bis[tetramethylethylene-bis(2-methylindenyl)-zirconium chloride], μ-oxo-bis[tetramethylethylene-bis(2-methyl-4,5-benzoindenyl)zirconium chloride], μ-oxo-bis[stetramethylethylene-bis(2-methyl-4-phenyl-indenyl)zirconium chloride], μ-oxo-bis[tetramethylethylene-bis(2-methy-4-naphthylindenyl)zirconium chloride], μ-oxo-bis[tetramethylethylene-bis(1-cyclopentaphenanthryl)zirconium chloride], μ-oxo-bis[tetramethylethylene-bis[1-( 2-methyl-cyclopenta)phenylindenyl)zirconium chloride]; μ-oxo-bis[tetramethylethylene-bis(3-tert-butylcyclopentadienyl)hafnium chloride], μ-oxo-bis[tetramethylethylene-bis(4-tert-butyl-2-methylcyclopentadienyl)hafnium chloride], μ-oxo-bis[tetramethylethylene-bis(3-tert-butyl-2,5-dimethylcyclopentadienyl)hafnium chloride]; μ-oxo-bis[tetramethylethylene-bis(3-phenylcyclopentadienyl)hafnium chloride], μ-oxo-bis[tetramethylethylene-bis(4-phenyl-2-methylcyclopentadienyl)hafnium chloride], μ-oxo-bis[tetramethylethylene-bis(3-phenyl-2,5-dimethylcyclopentadienyl)hafnium chloride]; μ-oxo-bis[tetramethylethylene-bis(tetrahydroindenyl)hafnium chloride], μ-oxo-bis[tetramethylethylene-bis(indenyl)hafnium chloride], μ-oxo-bis[tetramethylethylene-bis(2-methyhndenyl)hafnium chloride], μ-oxo-bis[tetramethylethylene-bis(2-methyl-4,5-benzoindenyl)hafnium chloride], μ-oxo-bis[tetramethylethylene-bis(2-methyl-4-phenylindenyl)hafnium chloride], μ-oxo-bis[tetramethylethylene-bis(2-methyl-4-naphtylindenyl)hafnium chloride], μ-oxo-bis[tetramethylethylene-bis(1-cyclopentaphenanthryl)hafnium chloride], μ-oxo-bis[tetramethylethylene-bis[1-(2-methylcyclopenta)phenanthryl)hafnium chloride]; μ-oxo-bis[tetramethyldisilane-bis(3-tert-butylcyclopentadienyl)zirconium chloride], μ-oxo-bis[tetramethyldisilane-bis[(4-tert-butyl-2-methylcyclopentadienyl)zirconium chloride], μ-oxo-bis[(tetramethyldisilane-bis(4-tert-butyl-2,5-dimethylcyclopentadienyl)zirconium chloride]; μ-oxo-bis[tetramethyldisilane-bis(3-phenylcyclopentadienyl)zirconium chloride], μ-oxo-bis[tetramethyldisilane-bis(4-phenyl-2-methylcyclopentadienyl)zirconium chloride]; μ-oxo-bis[tetramethyldisilane-bis(3-phenyl-2,5-dimethylcyclopentadienyl)zirconium chloride]; μ-oxo-bis[tetramethyldisilane-bis-(tetrahydroindenyl)zirconium chloride], μ-oxo-bis[tetramethyldisilane-bis(indenyl)-zirconium chloride], μ-oxo-bis[tetramethyldisilane-bis(2-methylindenyl)zirconium chloride], μ-oxo-bis[tetramethyldisilane-bis(2-methyl-4,5-benzoindenyl)zirconium chloride], μ-oxo-bis[tetramethyldisilane-bis(2-methyl-4-phenylindenyl)zirconium chloride], μ-oxo-bis[tetramethyldisilane-bis(2-methyl-4-phehylindenyl)zirconium chloride], μ-oxo-bis[tetramethyldisilane-bis(1-cyclopentaphenanthryl)zirconium chloride, μ-oxo-bis[tetramethyldisilane-bis[1-(2-methylcyclopentaphenanthryl]zirconium chloride]; μ-oxo-bis[tetramethyldisilane-bis(3-tert-butylcyclopentadienyl)hafnium chloride], μ-oxo-bis[tetramethyldisilane-bis(4-tert-butyl-2-methylcyclopentadienyl)hafnium chloride], μ-oxo-bis[tetramethyldisilane-bis(3-tert-butyl-2,5-dimethyl-cyclopentadienyl)hafnium chloride]; μ-oxo-bis[tetramethyldisilane-bis(3-phenylcyclopentadienyl)hafnium chloride], μ-oxo-bis[tetramethyldisilane-bis(4-phenyl-2-methyl-cyclopentadienyl)hafnium chloride], μ-oxo-bis[tetramethyldisilane-bis(3-phenyl-2,5-dimethylcyclopentadienyl)hafnium chloride]; μoxo-bis[tetramethyldisilane-bis-(tetrahydroindenyl)hafnium chloride], μ-oxo-bis[tetramethyldisilane-bis(indenyl)hafnium chloride], μ-oxo-bis[tetramethyldisilane-bis(2-methylindenyl)hafnium chloride], μ-oxo-bis[tetramethyldisilane-bis(2-methyl-4,5-benzoindenyl)hafnium chloride], μ-oxo-bis[tetramethyldisilane-bis(2-methyl-4-phtenylindenyl)hafnium chloride], μ-oxo-bis[tetramethyldisilane-bis(2-methyl-4-naphthylindenyl)hafnium chloride], μ-oxo-bis[tetramethyldisilane-bis(1-cyclopentaphenanthryl)hafnium chloride], tetramethyldisilane-bis[1-(2methylcyclopenta)phenanthryl]hafnium chloride]; μ-oxo-bis[diphenylsilylene-bis(3-tert-butylcyclopentadienyl)zirconium chloride], μ-oxo-bis[diphenylsilylene-bis(4-tert-butyl-2-methylcyclopentadienyl)zirconium chloride], μ-oxo-bis[diphenylsilylene-bis(3-tert-butyl-2,5-dimethylcyclopentadienyl)zirconium chloride]; μ-oxo-bis[diphenylsilylene-bis(3-phenylcyclopentadienyl)ziycoirum chloride], μ-oxo-bis[diphenylsilylene-bis(4-phenyl-2-methylcyclopentadienyl)zirconium chloride], μ-oxo-bis[diphenylsilylene-bis(3-phenyl-2,5-dimethylcyclopentadienyl)-zirconium chloride]; μ-oxo-bis[diphenylsilylene-bis(3-ethylphenylcyclopentadienyl)-zirconium chloride], μ-oxo-bis[diphenylsilylene-bis(4-ethylphenyl-2-methylcyclopentadienyl)zirconium chloride], μ-oxo-bis[diphenylsilylene-bis(3-ethypheny2,5-dimethylcyclopentadienyl)zirconium chloride]; μ-oxo-bis[diphenylsilylene-bis(3-fluorophenylcyclopentadienyl)zirconium chloride], μ-oxo-bis[diphenylsilylene-bis(4-fluorophenyl-2-methylcyclopentadienyl )zirconium chloride], μ-oxo-bis[diphenylsilylene-bis(3-fluorophenyl-2,5-dimethylcyclopentadienyl)zirconium chloride]; μ-oxo-bis[diphenylsilylene-bis(3-naphthylcyclopentadienyl)zirconium chloride], μ-oxo-bis[diphenylsilylene-bis(4-naphthyl-2-methylcyclopentadienyl)zirconium chloride], μ-oxo-bis[diphenylsilylene-bis(3-naphthyl-2,5-dimethylcyclopentadienyl)zirconium chloride]; μ-oxo-bis diphenylsilylene-bis(tetrahydroindenyl)zirconium chloride], μ-oxo-bis[diphenylsilylene-bis(indenyl)zirconium chloride], μ-oxo-bis[diphenylsilylene-bis(2-methylindenyl) zirconium chloride], μ-oxo-bis[diphenylsilylene-bis(2-methyl-4,5-benzoindenyl)zirconium chloride], μ-oxo-bis[diphenylsilylene-bis(2-methyl-4-phenylindenyl)zirconium chloride], μ-oxo-bis[diphenylsilylene-bis(2-methyl-4-naphthylindenyl)zirconium chloride], μ-oxo-bis[diphenylsilylene-bis(1-cyclopentaphenanthryl)zirconium choride], μ-oxo-bis[diphenylsilylene-bis[1-(2-cyclopenta)phenanthryl]zirconium chloride]; μ-oxo-bis[diphenylsilylene-bis(3-tert-butylcyclopentadienyl)hafnium chloride], μ-oxo-bis[diphenylsilylene-bis(4-tert-butyl-2-methylcyclopentadienyl)hafnium chloride], μ-oxo-bis[diphenylsilylene-bis(3-tert-butyl-2,5-dimethylcyclopentadienyl)hafnium chloride]; μ-oxo-bis[diphenylsilyene-bis(3-phenylcyclopentadienyl)hafnium chloride], μ-oxo-bis(diphenylsilylene-bis-(4-phenyl-2-methylcyclopentadienyl)hafnium chloride], μ-oxo-bis[diphenylsilylene-bis(3-phenyl-2,5-dimethylcyclopentadienyl)hafnium chloride]; μ-oxo-bis[diphenylsilylene-bis(3-ethylphenylcyclopentadienyl)hafnium chloride], μ-oxo-bis[diphenylsilylene-bis(4-ethylphenyl-2-methylcyclopentadienyl)hafnium chloride], μ-oxo-bis[diphenylsilyiene-bis(3-ethylphenyl-2,5-dimethylcyclopentadienyl)hafnium chloride]; μ-oxo-bis[diphenylsilylene-bis(3-fluorophenylcyclopentadienyl)hafnium chloride], μ-oxo-bis[diphenylsilylene-bis(4-fluorophenyl-2-methylcyclopentadienyl)hafnium chloride], μ-oxo-bis[diphenylsilylene-bis(3-fluorophenyl-2,5-dimethylcyclopentadienyl)hafnium chloride]; μ-oxo-bis[diphenylsilylene-bis(3-naphthylcyclopentadienyl)hafnium chloride], μ-oxo-bis[diphenylsilylene-bis(4-naphthyl-2-methylcyclopentadienyl)hafnium chloride], μ-oxo-bis[diphenylsilylene-bis(3-naphthyl-2,5-dimethylcyclopentadienyl)hafnium chloride]; μ-oxo-bis[diphenylsilylene-bis(tetrahydroindenyl)hafnium chloride], μ-oxo-bis[diphenylsilylene-bis(indenyl)hafnium chloride], μ-oxo-bis[diphenylsilylene-bis(2-methylindenyl)hafnium chloride], μ-oxo-bis[diphenylsilylene-bis(2-methyl-4,5-benzoindenyl)hafnium chloride], μ-oxo-bis[diphenylsilylene-bis(2-methyl-4-phenylindenyl)hafnium chloride], μ-oxo-bis[diphenylsilylene-bis(2-methyl-4-naphthylindenyl)hafnium chloride], μ-oxo-bis[diphenylsilylene-bis(1-cyclopentaphenanthryl)hafnium chloride], μ-oxo-bis[diphenylsilylene-bis-[1-(2-methylcyclopenta)phenanthryl]hafnium chloride]; μ-oxo-bis[methylphenylsilylene-bis(3-tert-butylcyclopentadienyl)zirconium chloride], μ-oxo-bis[methylphenylsilylene-bis(4-tert-butyl-2-methylcyclopentadienyl)zirconium chloride], μ-oxo-bis[methylphenylsilylene-bis(3-tert-butyl-2,5-dimethylcyclopentadienyl)zirconium chloride]; μ-oxo-bis[methylphenylsilylene-bis(-3-phenylcyclopentadienyl) zirconium chloride], μ-oxo-bis[methylphenylsilylene-bis(4-phenyl-2-methylcyclopentadienyl)zirconium chloride], μ-oxo-bis (methylphenylsilylene-bis[3-phenyl-2,5-dimethylcyclopentadienyl)zirconium chloride]; μ-oxo-bis[methylphenylsilylene-bis(3-ethyl-phenylcyclopentadienyl)zirconium chloride], μ-oxo-bis[methylphenylsilylene-bis(4-ethylphenyl-2-methylcyclopentadienyl)zirconium chloride], μ-oxo-bis[methylphenylsilylene-bis(3-ethylphenyl-2,5-dimethylcyclopentadienyl)zirconium chloride]; μ-oxo-bis[methylphenylsilylene-bis(3-fluorophenylcyclopentadienyl)zirconium chloride], μ-oxo-bis[methylphenylsilylene-bis(4-fluorophenyl-2-methylcyclopentadienyl)zirconium chloride], μ-oxo-bis[methylphenylsilylene-bis(3-fluorophenyl-2,5-dimethylcyclopentadienyl)zirconium chloride]; μ-oxo-bis[methylphenylsilylene-bis(3-naphthylcyclopentadienyl)zirconium chloride], μ-oxo-bis[methylphenylsilylene-bis(4-naphthyl-2-methylcyclopentadienyl)zirconium chloride], μ-oxo-bis[methylphenylsilylene-bis(3-naphthyl-2,5-dimethylcyclopentadienyl)zirconium chloride]; μ-oxo-bis[methylphenylsilylene-bis-(tetrahydroindenyl)zirconium chloride], μ-oxo-bis[methylphenylsilylene-bis(indenyl)zirconium chloride], μ-oxo-bis[methylphenylsilylene-bis(2-methylindenyl)zirconium chloride], μ-oxo-bis[methylphenylsilylene-bis(2-methyl-4,5-benzoindenyl)zirconium chloride], μ-oxo-bis[methylphenylsilylene-bis(2-methyl-4-phenylindenyl)zirconium chloride], μ-oxo-bis[methylphenylsilylene-bis( 2-methyl-4-naphthylindenyl)zirconium chloride], μ-oxo-bis[methylphenylsilylene-bis(1-cyclopentaphenanthryl)zirconium chloride], μ-oxo-bis[methylphenylsilylene-bis[1-(2-cyclopenta)phenanthryl]zirconium chloride]; μ-oxo-bis[methylphenylsilylene-bis(3-tert-butylcyclopentadienyl)hafnium chloride], μ-oxo-bis[methylphenylsilylene-bis(4-tert-butyl-2-methylcyclopentadienyl)hafnium chloride], μ-oxo-bis[methylphenylsilylene-bis(3-tert-butyl-2,5-dimethylcyclopentadienyl)hafnium chloride]; μ-oxo-bis[methylphenylsilylene-bis(3-phenylcyclopentadienyl) hafnium chloride], μ-oxo-bis[methylphenylsilylene-bis(4-phenyl-2-methylcyclopentadienyl)hafnium chloride], μ-oxo-bis[methylphenylsilylene-bis(3-phenyl-2,5-dimethylcyclopentadienyl)hafnium chloride]; μ-oxo-bis[methylphenylsilylene-bis(3-ethylphenylcyclopentadienyl) hafnium chloride], μ-oxo-bis[methylphenylsilylene-bis(4-ethylphenyl-2-methylcyclopentadienyl)hafnium chloride], μ-oxo-bis[methylphenylsilylene-bis(3-ethylphenyl-2,5-dimethylcyclopentadienyl)hafnium chloride]; μ-oxo-bis[methylphenylsilylene-bis(3-fluorophenylcyclopentadienyl) hafnium chloride], μ-oxo-bis[methylphenylsilylene-bis-(4-fluorophenyl-2-methylcyclopentadienyl)hafnium chloride], μ-oxo-bis[methylphenylsilylene-bis(3-fluorophenyl-2,5-dimethylcyclopentadienyl)hafnium chloride]; μ-oxo-bis[methylphenylsilylene-bis(3-naphthylcyclopentadienyl) hafnium chloride], μ-oxo-bis[methylphenylsilylene-bis(4-naphthyl-2-methylcyclopentadienyl)hafnium chloride], μ-oxo-bis[methylphenylsilyene-bis(3-napthyl-2,5-dimethylcyclopentadienyl)hafnium chloride]; μ-oxo-bis[methylphenylsilylene-bis(tetrahydroindenyl)hafnium chloride], μ-oxo-bis[methylphenylsilylene-bis(indenyl) hafnium chloride], μ-oxo-bis[methylphenylsilylene-bis(2-methylindenyl)hafnium chloride], μ-oxo-bis[methylphenylsilylene-bis(2-methyl-4,5-benzoindenyl) hafnium chloride], μ-oxo-bis[methylphenylsilylene-bis(2-methyl-4-phenylindenyl)hafnium chloride], μ-oxo-bis[methylphenylsilylene-bis(2-methyl-4-naphthylindenyl) hafnium chloride], μ-oxo-bis[methylphenylsilylene-bis(1-cyclopentaphenanthrylthafnium chloride], μ-oxo-bis[methylphenylsilylene-bis[1-(2-cyclopenta)phenanthryl] hafnium chloride]; μ-oxo-bis[diphenylgermylene-bis(3-tert-butylcyclopentadienyl)zirconium chloride], μ-oxo-bis[diphenylgermylene-bis(4-tert-butyl-2-methylcyclopentadienyl)zirconium chloride], μ-oxo-bis[diphenylgermylene-bis(3-tert-butyl-2,5-dimethylcyclopentadienyl)zirconium chloride]; μ-oxo-bis[diphenylgermylene-bis(3-phenylcyclopentadienyl) zirconium chloride], μ-oxo-bis[diphenylgermylene-bis(4-phenyl-2-methylcyclopentadienyl)zirconium chloride], μ-oxo-bis[diphenylgermylene-bis(3-phenyl-2,5-dimethylcyclopentadienyl)zirconium chloride]; μ-oxo-bis

[diphenylgermylene-bis(3-ethylphenylcyclopentadienyl) zirconium chloride], μ-oxo-bis[diphenylgermylene-bis(4-ethylphenyl-2-methylcyclopentadienyl)zirconium chloride], μ-oxo-bis[diphenylgermylene-bis(3-ethylphenyl-2,5-dimethylcyclopentadienyl)zirconium chloride]; μ-oxo-bis[diphenylgermylene-bis(3-fluorophenylcyclopentadienyl) zirconium chloride], μ-oxo-bis[diphenylgermylene-bis(4-fluorophenyl-2-methylcyclopentadienyl)zirconium chloride], μ-oxo-bis[diphenylgermylene-bis(3-fluorophenyl-2,5-dimethylcyclopentadienyl)zirconium chloride]; μ-oxo-bis[diphenylgermylene-bis(3-naphthylcyclopentadienyl)zirconium chloride], μ-oxo-bis[diphenylgermylene-bis(4-naphthyl-2-methyl-cyclopentadienyl)zirconium chloride], μ-oxo-bis[diphenylgermylene-bis(3-naphthyl-2,5-diethylcyclopentadienyl)zirconium chloride]; μ-oxo-bis[diphenylgermylene-bis-(tetrahydroindenyl)zirconium chloride], μ-oxo-bis(diphenylgermylene-bis(indenyl)zirconium chloride], μ-oxo-bis[diphenylgermylene-bis(2-methylindenyl)zirconium chloride], μ-oxo-bis[diphenylgermylene-bis(2-methyl-4,5-benzoindenyl)zirconium chloride], μ-oxo-bis[diphenylgermylene-bis(2-methy-4-phenylindenyl)zirconium chloride], μ-oxo-bis[diphenylgermylene-bis(2-methyl-4-naphthylindenyl)zirconium chloride], μ-oxo-bis[diphenylgermylene-bis(1-cyclopentaphenanthryl)zirconium chloride], μ-oxo-bis[diphenylgermylene-bis[1-(2-methylcyclopenta) phenanthryl)zirconium chloride]; μ-oxo-bis[diphenylgermylene-bis(3-tert-butylcyclopentadienyl)-hafnium chloride], μ-oxo-bis[diphenylgermylene-bis(4-tert-butyl-2-methylcyclopentadienyl)hafnium chloride], μ-oxo-bis[diphenylgermylene-bis(3-tert-butyl-2,5-dimethylcyclopentadienyl)hafnium chloride]; μ-oxo-bis[diphenylgermylene-bis(3-phenylcyclopentadienyl)hafnium chloride], μ-oxo-bis[diphenylgermylene-bis(4-phenyl-2-methylcyclopentadienyl)hafnium chloride], μ-oxo-bis[diphenylgermylene-bis(3-phenyl-2,5-dimethylcyclopentadienyl)hafnium chloride]; μ-oxo-bis[diphenylgermylene-bis(3-ethylphenylcyclopentadienyl)hafnium chloride], μ-oxo-bis[diphenylgermylene-bis(4-ethylphenyl-2-methylcyclopentadienyl)hafnium chloride], μ-oxo-bis[diphenylgermylene-bis(3-ethylphenyl-2,5-dimethylcyclopentadienyl)hafnium chloride]; μ-oxo-bis[diphenylgermylene-bis(3-fluorophenylcyclopentadienyl)hafnium chloride], μ-oxo-bis[diphenylgermylene-bis(4-fluorophenyl-2-methylcyclopentadienyl)hafnium chloride], μ-oxo-bis[diphenylgermylene-bis(3-fluorophenyl-2,5-dimethylcyclopentadienyl)hafnium chloride]; μ-oxo-biss(diphenylgermylene-bis(3-naphthylcyclopentadienyl)hafnium chloride], μ-oxo-bis[diphenylgermylene-bis(4-naphthyl-2-methylcyclopentadienyl)hafnium chloride], μ-oxo-bis[diphenylgermylene-bis(3-napthyl-2,5-dimethylcyclopentadienyl)hafnium chloride]; μ-oxo-bis[diphenylgermylene-bis(tetrahydroindenyl)hafnium chloride], μ-oxo-bis[diphenylgermylene-bis(indenyl)hafnium chloride], μ-oxo-bis[diphenylgermylene-bis(2-methylindenyl)hafnium chloride], μ-oxo-bis diphenylgermylene-bis(2-methyl-4,5-benzoindenyl)hafnium chloride], μ-oxo-bis[diphenylgermylene-bis(2-methyl-4-phenylindenyl)hafnium chloride], μ-oxo-bis[diphenylgermylene-bis(2-methyl-4-naphthylindenyl)hafnium chloride], μ-oxo-bis[diphenylgermylene-bis(1-cyclopentaphenanthryl)hafnium chloride], μ-oxo-bis[diphenylgermylene-bis[1-(2-cyclopenta)phenanthryl]hafnium chloride]; μ-oxo-bis[methylphenylgermylene-bis(3-tert-butylcyclopentadienyl)zirconium chloride], μ-oxo-bis[methylphenylgermylene-bis(4-tert-butyl-2-methylcyclopentadienyl)zirconium chloride], μ-oxo-bis[methylphenylgermylene-bis-(3-tert-butyl-2,5-dimethylcyclopentadienyl)zirconium chloride]; μ-oxo-bis[methylphenylgermylene-bis(3-phenylcyclopentadienyl) zirconium chloride], μ-oxo-bis[methylphenylgermylene-bis(4-phenyl-2-methylcyclopentadienyl)zirconium chloride], μ-oxo-bis[methylphenylgermylene-bis(3-phenyl-2,5-dimethylcyclopentadienyl)zirconium chloride]; μ-oxo-bis[methylphenylgermylene-bis(3-ethylphenylcyclopentadienyl)zirconium chloride], μ-oxo-bis[methylphenylgermylene-bis(4-ethylphenyl-2-methylcyclopentadienyl)zirconium chloride], μ-oxo-bis[methylphenylgermylene-bis-(3-ethylphenyl-2,5-dimethylcyclopentadienyl)zirconium chloride]; μ-oxo-bis[methylphenylgermylene-bis(3-fluorophenylcyclopentadienyl)zirconium chloride], μ-oxo-bis[methylphenylgermylene-bis(4-fluorophenyl-2-methylcyclopentadienyl)zirconium chloride], μ-oxo-bis[methylphenylgermylene-bis(3-fluorophenyl-2,5-dimethylcyclopentadienyl)zirconium chloride]; μ-oxo-bis[methylphenylgermylene-bis(3-naphthylcyclopentadienyl)zirconium chloride], μ-oxo-bis methylphenylgermylene-bis(4-naphthyl-2-methylcyclopentadienyl)zirconium chloride], μ-oxo-bis[methylphenylgermylene-bis(3-naphthyl-2,5-dimethylcyclopentadienyl)zirconium chloride]; μ-oxo-bis[methylphenylgermylene-bis(tetrahydroindenyl)zirconium chloride], μ-oxo-bis[methylphenylgermylene-bis(indenyl) zirconium chloride], μ-oxo-bis[methylphenylgermylene-bis(2-methylindenyl)zirconium chloride], μ-oxo-bis [methylphenylgermylene-bis(2-methyl-4,5-benzoindenyl)zirconium chloride], μ-oxo-bis[methylphenylgermylene-bis(2-methy-4-phenylindenyl)zirconium chloride], μ-oxo-bis[methylphenylgermylene-bis(2-methyl-4-naphtylindenyl) zirconium chloride], μ-oxo-bis[methylphenylgermylene-bis(2-cyclopentaphenadthryl)zirconium chloride], μ-oxo-bis[methylphenylgermylene-bis[1-(2-cyclopenta)phenanthryl) zirconium chloride]; μ-oxo-bis[methylphenylgermylene-bis(3-tert-butylcyclopentadienyl)hafnium chloride], μ-oxo-bis[methylphenylgermylene-bis(4-tert-butyl-2-methylcyclopentadienyl)hafnium chloride], μ-oxo-bis[methylphenylgermylene-bis(3-tert-butyl-2,5-dimethylmethylcyclopentadienyl)hafnium chloride]; μ-oxo-bis[methylphenylgermyene-bis(3-phenylcyclopentadienyl) hafnium chloride], μ-oxo-bis[methylphenylgermylene-bis (4-phenyl-2-methylcyclopentadienyl)hafnium chloride], μ-oxo-bis[methylphenylgermylene-bis(3-phenyl-2,5-dimethyl1cyclopentadienyl)hafnium chloride]; μ-oxo-bis[methylphenylgermylene-bis(3-ethylphenylcyclopentadienyl)hafnium chloride], μ-oxo-bis[methylphenylgermylene-bis(4-ethylphenyl-2-methylcyclopentdienyl)hafnium chloride], μ-oxo-bis[methylphenylgermylene-bis(3-ethylphenyl-2,5-dimethylcyclopentadienyl)hafnium chloride]; μ-oxo-bis(methylphenylgermylene-bis(3-ethylphenylcyclopentadienyl)hafnium chloride], μ-oxo-bis[methylphenylgermylene-bis(4-ethylphenyl-2-methylcyclopentadienyl)hafnium chloride], μ-oxo-bis[methylphenylgermylene-bis(3-ethylphenyl-2,5-dimethylcyclopentadienyl)hafnium chloride]; μ-oxo-bis[methylphenylgermylene-bis(3-fluorophenylcyclopentadienyl)hafnium chloride], μ-oxo-bis[methylphenylgermylene-bis(4-fluorophenyl-2-methylcyclopentadienyl)hafnium chloride], 9-oxo-bis[methylphenylgermylene-bis(3-fluorophenyl-2,5-dinethylcyclopentadienyl)hafnium chloride]; μ-oxo-bis[methylphenylgermylene-bis(3-naphthylcyclopentadienyl)hafnium chloride], μ-oxo-bis[methylphenylgermylene-bis (4-naphthyl-2-methylcyclopentadienyl)hafnium chloride], μ-oxo-bis[methylphenylgermylene-bis(3-naphthyl-2,5-dimethylcyclopentadienyl)hafnium chloride]; μ-oxo-bis[methylphenylgermylene-bis(tetrahydroindenyl)hafnium chloride], μ-oxo-bis[methylphenylgermylene-bis(indenyl) hafnium chloride], μ-oxo-bis[methylphenylgermylene-bis(2-methylindenyl)hafnium chloride], μ-oxo-bis[methyiphenylgermylene-bis(2-methyl-4,5-benzoindenyl) hafnium chloride], μ-oxo-bis[methylphenylgermylene-bis(2-methyl-4-phenylindenyl)hafnium chloride], μ-oxo-bis[methylphenylgermylene-bis(2-methyl-4-naphthylindenyl) hafnium chloride], μ-oxo-bis[methylphenylgermylene-bis(1-cyclopentaphenanthryl)hafnium chloride], μ-oxo-bis[methylphenylgermylene-bis[2-(2-cyclopenta)phenanthryl] hafnium chloride]; μ-oxo-bis[dimethylsilylene-bis[2-(2-furyl)-3,5-dimethylcyclopentadienyl]zirconium chloride], μ-oxo-bis[dimethylsilylene-bis[2-(2-furyl)-4,5-dimethylcyclopentadienyl]-zirconium chloride], μ-oxo-bis[dimethylsilylene-bis[2-(2-furyl)-indenyl]zirconium chloride], μ-oxo-bis[dimethylsiltlene-bis[2-(2-benzofuryl)-3,5-dimethylcyclopentadienyl]zirconium chloride], μ-oxo-bis[dimethylsilylene-bis[2-(2-benzofuryl)-4,5-dimethylcyclopentadienyl)zirconium chloride], and μ-oxo-bis[dimethylsilylene-bis[2-(2-benzofuryl)indenyl] zirconium chloride].

Likewise, illustrative of the compound wherein X stands for a substituent other than chlorine are, for example, μ-oxo-bis[dimethylsilylene-bis(2,3,5-trimethylcyclopentadienyl)zirconium methyl], μ-oxo-bis[dimethylsilylene-bis( 2,3,5-trimethylcyclopentadienyl) zirconium isopropyl], μ-oxo-bis[dimethylsilylene-bis(2,3,5-trimethylcyclopentadienyl)zirconium phenylacetylide], μ-oxo-bis[dimethylsilylene-bis(2-methyl-4-tert-butylcyclopentadienyl)zirconium methyl, μ-oxo-bis[dimethylsilylene-bis(2-methyl-4-tert-butylcyclopentadienyl)zirconium isopropyl, μ-oxo-bis[dimethylsilylene-bis(2-methyl-4-tert-butylcyclopentadienyl)zirconium phenylacetylide, μ-oxo-bis[dimethylsilylene-bis(2-methyl-4-tert-butylcyclopentadienyl)zirconium rimethylsilylacetylide; μ-oxo-bis[dimethylsilylene-bis(2-methyl-4-phenyl-4-hydroazulenyl)zirconium dichloride, and dimethylsilylene-bis(2-methyl-4-phenyl-4-hydroazulenyl)hafnium dichloride.

The μ-oxo-bis-metallocene complex compounds -of the present invention in combination with a cocatalyst become a highly active catalyst for polymerization of olefins and enables to obtain polyolefins with a narrow molecular weight distribution. The μ-oxo-bis-metallocene complex compounds can also be used in combination with other metallocene complex compounds. Examples of other components which constitute, in combination of the μ-oxo-bis-metallocene complex compound, a catalyst for the polymerization of olefms include at least one compound selected from an aluminoxane, an ionic compound capable of forming an ionic complex by reaction with the μ-oxo-bis-metallocene complex compounds and Lewis acids which are generally employed for polymerization of olefins. Above all, ail aluminoxane is most preferably used as cocatalyst.

The μ-oxo-bis-metallocene complex compound can be obtained, if necessary, by reacting a metallocene complex compound with water in the presence of a base. The substituent X in the resultant μ-oxo-bis-metallocene complex compound can further be converted into another substituent according to a method known per so to form a different μ-oxo-bis-metallocene complex compound from the aforesaid compound. In case X in the μ-oxo-bis-metallocene complex compound is chlorine, for example, the compound can be converted by reacting itself with methyl lithium in an equivalent amount of the chlorine to form the μ-oxo-bis-metallocene complex compound of the present invention wherein X stands for methyl group.

The aluminoxane referred to herein are an organoaluminum compound represented by the formula (6) or (7):

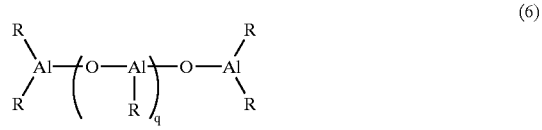

wherein R's may be the same or different and each stands for a hydrocarbon group having 1–20, preferably 1–4 carbon atoms, in particular, methyl group, ethyl group, propyl group, isopropyl group, butyl group, or isobutyl group, and q stands for an integer of 1–1000 with the proviso that the value of q may be different to form a mixture of the compounds.

The ionic compound referred to herein is a salt of a cationic compound and an anionic compound. Examples of the anion include an anion of an organoboron compound and an anion of an organoaluminum compound. Examples of the cation include a metal cation, a cation of an organometallic compound, carbonium cation, tropium cation, oxonium cation, sulfonium cation, phosphonium cation, and ammonium cation. Among these, an ionic compound involving boron is preferable as the anion. More particularly, there are mentioned N,N-dimethylanilium tetrakis-(pentafluorophenyl)borate and trimethyl tetrakis (pentafluorophenyl)borate.

The Lewis acid referred to herein is preferably a Lewis acid containing born atom. More precisely mentioned are tri(n-butyl) boron, triphenylboron, tris[3,5-bis-(trifluoromethyl)phenyl]boron, tris[(4-fluoromethyl)phenyl] boron, tris(3,5-difluorophenyl)boron, tris(3,5-difluorophenyl)boron, tris(2,4,6-trifluorophenyl)boron, tris-(pentafluorophenyl)boron, etc.

As ionic compounds and Lewis acids other than the aforementioned, those disclosed in Japanese published and searched Patent Appln. No. Hei. 1-501950, Japanese published and searched Patent Appln. No. Hei. 1-502036, Japanese Laid-open Patent Appln. No. Hei. 3-179006, Japanese Laid-open Patent Appln. No. Hei. 3-207703 and Japanese Laid-open Patent Appln. No. Hei. 3-207704 can also be used.

A proportion of the μ-oxo-bis-metallocene complex compound to be used to these other catalyst components to be used is such that 1 in case the aluiminoxane is used as the catalyst component, 1–50,000 moles, preferably 50–20,000 moles of the Al atom in the aluminoxane are used per mole of the metal atom of the μ-oxo-bis-metallocene complex compound.

A proportion of the μ-oxo-bis-metallocene complex compound to be used to the ionic compound or Lewis acid as the other catalyst component to be used is such that 0.01–2,000 moles, preferably 0.1–599 moles of the ionic compound or Lewis acid is used per mole of the metal atom of the p-oxo-bis-metallocene complex compound.

The μ-oxo-bis-metallocene complex compound of the present invention may be used as a supported-type catalyst carried on a particulate support. A granular or spherical inorganic or organic particulate solid having a particle diameter of 5–300 μm, preferably 10–200 μm is used as such particulate support.

The particulate inorganic support is preferably a metal oxide, for example, $SiO_2$, $Al_2O_3$, MgO, $TiO_2$, ZnO or a mixture of these, and more preferably a support containing as a predominant component at least one selected from the group consisting of $SiO_2$, $A_2O_3$ and MgO. More precisely mentioned are $SiO_2$, $Al_2O_3$, MgO, $SiO_2$—$Al_2O_3$, $SiO_2$—MgO, $SiO_2$—$TiO_2$ and $SiO_2$—$Al_2O_3$ —MgO. These inorganic oxide supports are used usually by baking at 100–1000° C. for 1–40 hours.

Mentioned as the organic particulate support are polymers or copolymers of α-olefins having 2–12 carbon atoms* such as ethylene, propylene, 1-butene and 4-methyl-1-pentene, and polymers or copolymers of styrene or a derivatives thereof.

Illustrative of olefins which are polymerizale by the aid of a catalyst comprised essentially of the μ-oxo-bis-metallocene complex compound and the cocatalyst of the present invention are a linear α-olefin such as ethylene, propylene, 1-butene, 4-methyl-1-pentene, 1-hexene, 1-oetene, 1-decene, 1-dodecene, 1-tetradecene, 1-hexadecene, 1-octadecene or 1-eicocene, a branched chain α-olefin olefin such as 3-methyl-1-butene, 4-methyl-1-pentene or 2-methyl-1-pentene, and a mixture of at least two of these.

α-olefin polymers obtained by the aid of the catalyst of of the present invention containing the μ-oxo-bis-metallocene complex compound are not only homopolymers of the aforesaid olefins but also co- or terpolymers of olefins mutually combined or combined with others, for example, a combination of two such as ethylene with propylene, or a combination of three such as ethylene, propylene and 1-butene and block copolymers of olefins formed by changing the sort of fed olefins at every stage of a multi-stage polymerization.

A Polymerization or copolymerization of cyclic olefins, dienes, styrenes, and other polymerizable monomers having double bond or bonds with α-olefins by the aid of the aforesaid catalyst. Illustrative of the cyclic olefins are, for example, cyclobutene, cyclopentene, cyclohexene, cycloheptene, norbornene, 5-ethyl-2-norbornene, phenylnorbornene, and indanylnorbornene. Illustrative of the dienes are, for example, cyclic dienes such as 5-methylene-2-norbornene, 5-ethylidene-2-norbornene, 5-propylidene-5-norbornene, dicyclopentadiene, and 5-vinyl-2-norbornene as well as chain dienes such as 1,3-butadiene, isoprene, 1,4-hexadiene, 4-methyl-1,4-hexadiene, 5-methyl-1,4-hexadiene, 5-methyl-1,5-heptadiene, 6-methyl-1,5-heptadiene, 1,7-octadiene, 6-methyl-1,7-octadiene, 7-methyl-1,6-octadiene, 1,8-nonadiene and 1,9-decadiene.

Illustrative of the styrenes are, for example, styrene itself, p-chlorostyrene, p-methylstyrene, p-tert-butylstyrene, α-methylstyrene and vinylnaphthalene. Illustrative of the other polymerizable monomers having double bond or bonds are, for example, vinylcyclohexane, vinyl chloride, 4-trimethylsiloxy-1,6-heptadiene, 5-(N,N-diisopropylamino)-1-pentene, methyl methacrylate and ethyl acrylate.

Either of liquid polymerization or vapor phase polymerization can be adopted for a process for the polymerization of olefins by the aid of a catalyst containing the μ-oxo-bis-metallocene complex compound of the present invention. In the liquid polymerization, an inert hydrocarbon may be used as solvent and a liquefied olefin per se such as liquefied propylene or liquefied 1-butene may also be used as solvent. An aromatic hydrocarbon such as benzene, toluene, ethylbenzene or xylene; an aliphatic hydrocarbon such as butane, isobutane, pentane, hexane, heptane, octane, decane, dodecane, hexadecane or octadecane; an alicyclic hydrocarbon such as cyclopentane, methylcyclopentane, cyclohexane, cycloheptane or cyclooctane; and a petroleum fraction such as gasoline, kerosene or light oil can be mentioned as a polymerization solvent.

A polymerization process may be either of a batchwise, semi-continuous or continuous method, and may be carried out in at least two steps by changing the reaction condition in every step.

No particular limitation exists in the concentration of the metallocene compound in the polymerization reaction system in the polymerization process employing the catalyst containing the μ-oxo-bis-metallocene complex compound. The concentration is nevertheless preferable within the range of $10^{-2}$–$10^{-3}$ mol/l in terms of transition metal concentration.

No particular limitation also exists in pressure of olefin in the polymerization reaction system. A preferable range is however from atmospheric pressure to 50 kg/cm². Likewise, no particular limitation exists in polymerization temperature, but the temperature is usually within the range from –50° C. to 250° C., preferably from –30° C. to 100° C. Regulation of the molecular weight in the course of the reaction can be carried out in a known method, for example, by selecting the temperature or introduction of hydrogen.

EXAMPLES

The present invention will now be illustrated by way of Examples.

All of the reactions was carried out in an inert gas atmosphere. Reagents and solvents used in the syntheses are wholly those available commercially and actually employed without dehydrating treatment, while the reagents and solvents used for polymerization were previously dried.

Example 1
{Synthesis of μ-oxo-bis-[Dimethylsilylene-bis(2,3,5-trimethylcyclopentadienyl)zirconium Chloride]}

In a 100 ml reaction vessel made of glass were placed 210 mg (0.5 mmole) of an isomeric mixture (the racemic form/the meso form=50/50) of dimethylsilylene-bis(2,3,5-trimethylcyclopentadienyl)zirconium dichloride and 20 ml of toluene. To this mixture was added dropwise 0.5 ml (0.25 mmole) of a solution of triethylamine-toluene (0.5 mole/liter) at room temperature. It was confirmed according to NMR analysis that a ratio of the racemic form to the meso form was 75/15.

The reaction mixture was concentrated by distilling the solvent under reduced pressure, and 50 ml of hexane was added and thereafter the mixture was allowed to stand overnight. The mixture was filtered to collect 98 mg of the residue which was the μ-oxo-complex compound and triethylamine hydrochloride. The residue was extracted with toluene-hexane and filtered to remove insoluble triethyamine hydrochloride. The filtrate was concentrated by distilling the solvent under reduced pressure, hexane was then added and the mixture was cooled down to 20° C. and allowed to stand for one day. The crystals precipitated were collected by filtration, washed with hexane and then dried to obtain 30 mg of μ-oxo-bis[dimethylsilylene-bis(2,3,5- trimethylcyclopentadienyl)zirconium chloride] as colorless crystals. A structure of the complex compound was determined by $^1$H-NMR measurement, elementary analysis and single crystal X-ray diffraction. A result of the NMR measurement and the elementary analysis is shown in Table 1.

Example 2

{Synthesis of $\mu$-oxo-bis[silacyclopentane-bis(2,3,5-trimethylcyclopentadienyl)zirconnium chloride]}

In a 100 ml reaction vessel made of glass were placed 190 mg (0.44 mmole) of an isomeric mixture (the racemic form/the meso form=40/60) of silacyclopentane-bis(2,3,5-trimethylcyclopentadienyl)zirconium dichloride and 20 ml of toluene. To this mixture was added dropwise 0.55 ml (0.28 mmole) of a solution of diethylamine-toluene (0.5 mole/liter) at room temperature. It was confirmed according to NMR analysis that a ratio of the racemic form to the meso form was 93/7.

The reaction mixture was concentrated by distilling the solvent under reduced pressure, and 50 ml of hexane was added and thereafter the mixture was allowed to stand overnight. The mixture was filtered to collect 80 mg of the residue which was the $\mu$-oxo-complex compound and diethylamine hydrochloride. The residue was extracted with toluene-hexane and filtered to remove insoluble diethyamine hydrochloride. The filtrate was concentrated by distilling the solvent under reduced pressure, hexane was then added and the mixture was cooled down to −20° C. and allowed to stand for one day. The crystals precipitated were collected by filtration, washed with hexane and then dried to obtain 30 mg of $\mu$-oxo-bis[silacyclopentane-bis(2,3,5-trimethylcyclopentadienyl)zirconium chloride] as colorless crystals. A structure of the complex compound was determined by $^1$H-NMR measurement, elementary analysis and single crystal X-ray diffraction. A result of the NMR measurement and the elementary analysis is shown in Table 1.

Example 3

{Synthesis of $\mu$-oxo-bis-[Dimethylsilylene-bis(3-tert-butylcyclopentadienyl)zirconium Chloride]}

In a 100 ml reaction vessel made of glass were placed 230 mg (0.5 mmole) of an isomeric mixture (the racemic form/the meso form=40/60) of dimethylsilylene-bis(3-tert-butylcyclopentadienyl)zirconium dichloride and 20 ml of toluene. To this mixture was added dropwise 0.5 ml (0.25 mmole) of a solution of triethylamine-toluene (0.5 mole/liter) at room temperature. It was confirmed according to NMR analysis that a ratio of the racemic form to the meso form was 68/32.

The reaction mixture was concentrated by distilling the solvent under reduced pressure, and 50 ml of hexane was added and thereafter the mixture was allowed to stand overnight. The mixture was filtered to collect 63 mg of the residue which was the $\mu$-oxo-complex compound and triethylamine hydrochloride. The residue was extracted with toluene-hexane and filtered to remove insoluble triethylamine hydrochloride. The filtrate was concentrated by distilling the solvent under reduced pressure, hexane was then added and the mixture was cooled down to 20° C. and allowed to stand for one day. The crystals precipitated were collected by filtration, washed with hexane and then dried to obtain 29 mg of $\mu$-oxo-bis[dimethylsilylene-bis(3-tert-butylcyclopentadienyl)zirconium chloride) as colorless crystals. A result of the NMR measurement and the elementary analysis is shown in Table 1.

Example 4

{Synthesis of $\mu$-oxo-bis-[Dimethylgermylene-bis(2,3,5-trimethylcyclopentadienyl)zirconium Chloride]}

In a 100 ml reaction vessel made of glass were placed 240 mg (0.5 mmole) of an isomeric mixture (the racemic form/the meso form=50/50) of dimethylgermylene-bis(2,3,5-trimethylcyclopentadienyl)zirconium dichloride and 20 ml of toluene. To this mixture was added dropwise 0.5 ml (0.25 mmole) of a solution of triethylamine-toluene (0.5 mole/liter) at room temperature. It was confirmed according to NMR analysis that a ratio of the racemic form to the meso form was 87/13.

The reaction mixture was concentrated by distilling the solvent under reduced pressure, and 50 ml of hexane was added and thereafter the mixture was allowed to stand overnight. The mixture was filtered to collect 71 mg of the residue which was the $\mu$-oxo-complex compound and triethylamine hydrochloride. The residue was extracted with toluene-hexane and filtered to remove insoluble triethyamine hydrochloride. The filtrate was concentrated by distilling the solvent under reduced pressure, hexane was then added and the mixture was cooled down to 20° C. and allowed to stand for one day. The crystals precipitated were collected by filtration, washed with hexane and then dried to obtain 31 mg of $\mu$-oxo-bis[dimethylgermylene-bis(2,3,5-trimethylcyclopentadienyl)zirconium chloride] as colorless crystals. A result of the NMR measurement and the elementary analysis is shown in Table 1.

Example 5

{Synthesis of $\mu$-oxo-bis-[Dimethylgermylene-bis(2,3,5-trimethylcyclopentadienyl)hafnium Chloride]}

In a 100 ml reaction vessel made of glass were placed 280 mg (0.5 mmole) of an isomeric mixture (the racemic form/the meso form=50/50) of dimethylgermylene-bis(2,3,5-trimethylcyclopentadienyl)hafnium dichloride and 20 ml of toluene. To this mixture was added dropwise 0.5 ml (0.25 mmole) of a solution of triethylamine-toluene (0.5 mole/liter) at room temperature. It was confirmed according to NMR analysis that a ratio of the racemic form to the meso form was 68/32.

The reaction mixture was concentrated by distilling the solvent under reduced pressure, 50 ml of hexane was added and the mixture was allowed to stand overnight and then filtered to remove the precipitated triethylamine hydrochloride. The filtrate was concentrated by distilling the solvent under reduced pressure, toluene was added to dissolve the residue and hexane was then added. The mixture was cooled down to 20° C. and allowed to stand for one day. The crystals precipitated were collected by filtration, washed with hexane and then dried to obtain 31 mg of $\mu$-oxo-bis[dimethylgermylene-bis(2,3,5-trimethylcyclopentadienyl)hafnium chloride] as colorless crystals. A result of the NMR measurement and the elementary analysis is shown in Table 1.

Example 6

{Synthesis of $\mu$-oxo-bis-[Dimethylgermylene-bis(2,4-dimethylcyclopentadienyl)zirconium Chloride]}

In a 100 ml reaction vessel made of glass were placed 220 mg (0.5 mmole) of an isomeric mixture (the racemic form/the meso form=10/90) of dimethylgermylene-bis(2,4-dimethylcyclopentadienyl)zirconium dichloride and 10 ml of toluene. To this mixture was added dropwise 0.9 ml (0.45 mmole) of a solution of triethylamine-toluene (0.5 mole/liter) at room temperature.

The reaction mixture was concentrated by distilling the solvent under reduced pressure, 50 ml of hexane was added and the mixture was allowed to stand overnight and then filtered to remove the precipitated triethylamine hydrochloride.

The filtrate was concentrated by distilling the solvent under reduced pressure, toluene was added to dissolve the residue and hexane was then added. The mixture was cooled down to 20° C. and allowed to stand for one day. The crystals precipitated were collected by filtration, washed with hexane and then dried to obtain 6 mg of μ-oxo-bis [dimethylgermylene-bis(2,4-dimethylcyclopentadienyl) zirconium chloride] as colorless crystals. A result of the NMR measurement and the elementary analysis is shown in Table 1.

Example 7

{Synthesis of μ-oxo-bis[Dimethylsilylene-bis(2,3,5-trimethylcyclopentadienyl)zirconium Chloride]

In a 100 ml reaction vessel made of glass were placed 210 mg (0.5 mmole) of an isomeric mixture (the racemic form/ the meso form=50/50) of dimethylgermylene-bis(2,4-dimethylcyclopentadienyl)zirconium dichloride and 10 ml of toluene. To this mixture was added dropwise 0.7 ml (1.0 mmole) of a solution of methyllithium-di-ethyl ether (1.41 mole/liter) at 0° C. The mixture was stirred for 15 minutes at room temperature and then the mixture was filtered to remove the lithium salt.

The reaction mixture was concentrated by distilling the solvent under reduced pressure, toluene was added to dissolve the residue, and hexane was then added. The mixture was cooled down to −20° C. and allowed to stand for one day. The crystals precipitated were collected by filtration washed with hexane and then dried to obtain 25 mg of μ-oxo-bis[dimethylsilylene-bis(2,3,5-trimethylcyclopentadienyl)zirconium chloride] as colorless crystals. A result of the NMR measurement and the elementary analysis is shown in Table 1.

Example 8

{Synthesis of μ-oxo-bis [Dimethylsilylene-bis(2,3,5-trimethylcyclopentadienyl)zirconium Phenylacetylide]}

In a 100 ml reaction vessel made of glass were placed 0.1 g (1.0 mmole) of phenylacetylene and 10 ml of THF. The vessel was cooled to 10° C. and 0.64 ml (1.0 mmole) of a solution of n-butyllithium-hexane (1.56 mole/liter) was added dropwise to the mixture. At room temperature the mixture was stirred for 1 hour. Separately, in a 100 ml Kjeldahl flask was placed 0.21 g (0.5 mmole) of μ-oxo-bis [dimethylsilylene-bis(2,3,5-trimethylcyclopentadienyl) sirconium chloride], and 10 ml of THF was added to dissolve the complex compound. The mixture was cooled to 0° C. and the solution previously prepared was added dropwise thereto and the whole was stirred for one hour at room temperature. The solvents were distilled off under reduced pressure, 10 ml of toluene was added and insoluble lithium salt was filtered off. The solvents of the filtrate was distilled off under reduced pressure, and toluene was added to dissolve the residue. Hexane was the added and the mixture was cooled down to −20° C. and allowed to stand for one day. The crystals precipitated were collected by filtration, washed with hexane and then dried to obtain 120 mg (yield: 51%) of μ-oxo-bis (dimethylsilylene-bis(2,3,5-trimethylcyclopentadienyl)zirconium phenylacetylide] as orange crystals. A result of the NMR measurement and the elementary analysis is shown in Table 1.

IR (KBr): $v_c\equiv_c 2077$ cm$^{-1}$.

Example 9

{Synthesis of μ-oxo-bis[Dimethylsilylene-bis(2,3,5-trimethylcyclopentadienyl)zirconium Trimethylsilylacetylide]}

In a 100 ml reaction vessel made of glass were placed 0.1 g (1.0 mmole) of trimethylsilylacetylene and 10 ml of THF. The vessel was cooled to 10° C. and 0.64 ml (1.0 mmole) of a solution of n-butyllithium-hexane (1.56 mole/liter) was added dropwise to the mixture. At room temperature the mixture was stirred for 1 hour. in a separate 100 ml Kjeldahl flask was placed 0.21 g (0.5 mmole) of μ-oxo-bis [dimethylsilylene-bis(2,3,5-trimethylcyclopentadienyl) sirconium chloride], and 10 ml of THF was added to dissolve the complex compound. The mixture was cooled to 0° C. and the solution previously prepared was added dropwise thereto and the whole was stirred for one hour at room temperature. The solvents were distilled off under reduced pressure, 10 ml of toluene was added and insoluble lithium salt was filtered off. The solvents of the filtrate was distilled off under reduced pressure, and toluene was added to dissolve the residue. Hexane was the added and the mixture was cooled down to −20° C. and allowed to stand for one day. The crystals precipitated were collected by filtration, washed with hexane and then dried to obtain 60 mg (yield: 24%) of μ-oxo-bis[dimethylsilylene-bis(2,3,5-trimethylcyclopentadienyl)zirconium trimethylsilylacetylide] as yellow crystals. A result of the NMR measurement and the elementary analysis is shown in Table 1.

IR (KBr): $v_c\equiv_c 2028$ cm$^{-1}$.

Example 10

{Synthesis of μ-oxo-bis-[Dimethylsilylene-bis(2-(2-furyl)-3,5-dimethylcyclopentadienyl)zirconium Chloride]}

In a 100 ml reaction vessel made of glass were placed 370 mg (0.7 mmole) of an isomeric mixture (the racemic form/ the meso form=14/86) of dimethylsilylene-bis[2-(2-furyl)-3,5-dimethylcyclopentadienyl)zirconium dichloride and 20 ml of toluene. To this mixture was added dropwise 2.2 ml (0.60 mmole) of a solution of triethylamine-toluene (0.27 mole/liter) at room temperature.

The reaction mixture was concentrated by distilling the solvent under reduced pressure, 5 ml of toluene and 15 ml of hexane was added and the mixture was allowed to stand overnight and then filtered to remove the precipitated triethylamine hydrochloride. The filtrate was concentrated by distilling the solvent under reduced pressure, toluene was added to dissolve the residue and hexane was then added. The mixture was cooled down to 20° C. and allowed to stand for one day. The crystals precipitated were collected by filtration, washed with hexane and then dried to obtain 30 mg of μ-oxo-bis (dimethylsilylene-bis(2-(furyl)-3,5-dimethylcyclopentadienyl)zirconium chloride) as colorless crystals. A structure of the complex compound was determined by H-NMR measurement. A result of the NMR measurement and the elementary analysis is shown in Table 1.

Example 11

{Polymerization of Propylene by the Aid of μ-oxo-bis [Dimethylsilylene-bis(2,3,5-trimethylcyclopentadienyl) zirconium Chloride]}

In a 100 ml container made of glass the air in which had been replaced with nitrogen was placed a solution of methylaluminoxane (manufactured by Toso-Akzo Corp.) in toluene in an amount such that a ratio of Al/Zr might be 10000. To this solution was added 1 ml (1.61×10$^{-6}$ mol) of a solution of μ-oxo-bis [dimethylsilylene-bis(2,3,5-trimethylcyclopentadienyl)zirconium chloride] in toluene, and the mixture was stirred for 30 minutes at room temperature. This solution was introduced into an autoclave made of SUS in which one liter of toluene had been contained, and the contents was heated at 30° C. Propylene was then introduced into the autoclave under pressure of 0.3 MPa and the polymerization reaction was carried out for one hour. After completion of the polymerization, the contents were filtered and the solvent in the filtrate was distilled off under reduced pressure. The remaining liquid was treated with methanol acidified with hydrochloric acid to decompose the catalyst components. The mixture was collected by filtration, and successively washed and dried to obtain 7.2 g of polypropylene.

A polymerization activity per gram of zirconium was calculated as 4.5 kg—PP/mmole—Zr —hr.

The resultant polypropylene had a Mw of 731000, a Mw/Mn of 2.45 and an mmmm of 0.196. An analytical data of the resultant polypropylene is shown in Table 2.

Example 12

{Polymerization of Ethylene by the Aid of μ-oxo-bis[Dimethylsilylene-bis(2,3,5-trimethylcyclopentadienyl)zirconium Chloride]}

In a 1500 ml autoclave made of SUS in which the air had been replaced with nitrogen was placed a solution of methylaluminxane (manufactured by Toso-Akzo Corp.) in toluene in an amount such that a ratio of Al/Zr might be 15000. To this solution was added 1 ml ($0.47 \times 10^{-6}$ mole) of a solution of μ-oxo-bis[dimethylsilylene-bis(2,3,5-trimethylcyclopentadienyl)zirconium chloride] in toluene, and the mixture was heated at 70° C. Ethylene was then introduced into the autoclave under pressure of 0.3 MPa and the polymerization reaction was carried out for 30 minutes. After completion of the polymerization, the resultant polyethylene was collected by filtration and treated with 2 liters of methanol acidified with hydrochloric acid to decompose the catalyst components. The solid was collected by filtration and successively washed and dried to obtain 20.2 g of polyethylene.

A polymerization activity per gram of zirconium was calculated as 86 kg—PE/mmole—Zr—hr.

The resultant polyethylene had a Mw of 101000, a Mw/Mn of 2.03 and a Mp of 135.8° C. An analytical data of the resultant polyethylene is shown in Table 3.

Example 13

{Polymerization of Propylene by the Aid of μ-oxo-bis[Silacyclopentane-bis(2,3,5-trimethylcyclopentadienyl)zirconium Chloride]}

In the same manner as described in Example 11, polymerization of propylene was carried out by the aid of μ-oxo-bis [silacyclopentane-bis(2,3,5-trimethylcyclopentadienyl)zirconium chloride].

An analytical data of the resultant polypropylene is shown in Table 2.

Example 14

{Polymerization of Ethylene by the Aid of μ-oxo-bis[Silacyclopentane-bis(2,3,5-trimethylcyclopentadienyl)zirconium Chloride]}

In the same manner as described in Example 12, polymerization of ethylene was carried out by the aid of μ-oxo-bis[silacyclopentane-bis(2,3,5-trimethylcyclopentadienyl)zirconium chloride].

An analytical data of the resultant polyethylene is shown in Table 3.

Example 15

{Polymerization of Ethylene by the Aid of μ-oxo-bis[Dimethylsilylene-bis(3-tert-butylcyclopentadienyl)zirconium Chloride]}

In the same manner as described in Example 12, polymerization was carried out by the aid of μ-oxo-bis[dimethylsilylene-bis(3-tert-butylcyclopentadienyl)zirconium chloride].

An analytical data of the resultant polyethylene is shown in Table 3.

Example 16

{Polymerization of Propylene by the Aid of μ-oxo-bis[Dimethylgermylene-bis(2,3,5-trimethylcyclopentadienyl)zirconium Chloride]}

In the same manner as described in Example 11, polymerization of propylene was carried out by the aid of μ-oxo-bis[dimethylgermylene-bis(2,3,5-trimethylcyclopentadienyl)zirconium chloride].

An analytical data of the resultant polypropylene is shown in Table 2.

Example 17

{Polymerization of Ethylene by the Aid of μ-oxo-bis[Dimethylgermylene-bis(2,3,5-trimethylcyclopentadienyl)zirconium Chloride]}

In the same manner as described in Example 12, polymerization of ethylene was carried out by the aid of μ-oxo-bis[dimethylgermylene-bis(2,3,5-trimethylcyclopentadienyl)zirconium chloride].

An analytical data of the resultant polyethylene is shown in Table 3.

Example 18

{Polymerization of Propylene by the Aid of μ-oxo-bis[Dimethylgermylene-bis(2,3,5-trimethylcyclopentadienyl)hafnium Chloride]}

In the same manner as described in Example 11, polymerization of propylene was carried out by the aid of μ-oxo-bis[dimethylgermylene-bis(2,3,5-trimethylcyclopentadienyl)hafnium Chloride].

An analytical data of the resultant polypropylene is shown in Table 2.

Example 19

{Polymerization of Ethylene by the Aid of μ-oxo-bis[Dimethylgermylene-bis(2,3,5-trimethylcyclopentadienyl)hafnium Chloride]}

In the same manner as described in Example 12, polymerization of ethylene was carried out by the aid of μ-oxo-bis[dimethylgermylene-bis(2,3,5-trimethylcyclopentadienyl)hafnium chloride].

An analytical data of the resultant polyethylene is shown in Table 3.

Example 20

{Polymerization of Propylene by the Aid of μ-oxo-bis[Dimethylsilylene-bis(2-(2-furyl)-3,5-dimethylcyclopentadienyl)hafnium Chloride]}

In the same manner as described in Example 11, polymerization of propylene was carried out by the aid of μ-oxo-bis[dimethylsilylene-bis(2-(2-furyl)-,3,5-dimethylcyclopentadienyl)hafnium chloride].

An analytical data of the resultant polypropylene is shown in Table 2.

Comparative Example 1

{Polymerization of Propylene by the Aid of μ-oxo-bis[bis(Cyclopentadienyl)zirconium Chloride]}

In the same manner as described in Example 11, polymerization of propylene was carried out by the aid of μ-oxo-bis (bis(cyclopentadienyl)zirconium chloride).

An analytical data of the resultant polypropylene is shown in Table 2.

Industrial Utilizability

The μ-oxo-bis-metallocene complex compounds provided according to the present invention are excellent in crystallinity and capable of being isolated easily, and can thus be utilized for the polymerization of olefins.

TABLE 1

Analytical data of the μ-oxo-bis-metallocene complex compounds

|  | $^1$H-NMR Spectra (CDCl$_3$; ppm) | Elementary Analysis (wt %) Calc. | Found |
|---|---|---|---|
| Example 1 {Me$_2$Si(2,3,5-Me$_3$Cp)$_2$ZrCl}$_2$O | 0.81(6H, s), 0.95(6H, s), 1.85(12H, s), 2.20(12H, s), 2.42(12H, s), 6.20(4H, s) | C: 53.35 H: 6.42 | C: 52.96 H: 6.50 |
| Example 2 {C$_4$H$_8$Si(2,3,5-Me$_3$Cp)$_2$ZrCl}$_2$O | 1.43(4H, t, J=7Hz), 1.57(4H, t, J=7Hz), 1.79–1.78(8H, m), 1.83(12H, s), 2.20(12H, s), 2.39(12H, s), 6.21(4H, s) | C: 55.71 H: 6.55 | C: 55.87 H: 6.54 |
| Example 3 {Me$_2$Si(3-t-BuCp)$_2$ZrCl}$_2$O | 0.72(6H, s), 0.73(6H, s), 1.31(36H, s), 5.48(4H, t, J=2Hz), 5.97(4H, t, J=3Hz), 6.31(4H, t, J=2Hz) | C: 55.49 H: 6.94 | C: 55.75 H: 6.94 |
| Example 4 {Me$_2$Ge(2,3,5-Me$_3$Cp)$_2$ZrCl}$_2$O | 0.96(6H, s), 1.10(6H, s), 1.83(12H, s), 2.20(12H, s), 2.40(12H, s), 6.17(4H, s) | C: 48.10 H: 5.79 | C: 48.36 H: 5.77 |
| Example 5 {Me$_2$Ge(2,3,5-Me$_3$Cp)$_2$HfCl}$_2$O | 0.97(6H, s), 1.10(6H, s), 1.90(12H, s), 2.23(12H, s), 2.48(12H, s), 6.13(4H, s) | C: 40.26 H: 4.88 | C: 40.76 H: 4.88 |
| Example 6 {Me$_2$Ge(2,4-Me$_3$Cp)$_2$ZrCl}$_2$O | 0.63(6H, s), 1.10(6H, s), 2.27(12H, s), 2.34(12H, s), 4.92(4H, d, J=2Hz), 6.23(4H, d, J=2Hz) | C: 45.58 H: 5.26 | C: 45.81 H: 5.26 |
| Example 7 {Me$_2$Si(2,3,5-Me$_3$Cp)$_2$ZrMe}$_2$O | −0.38(6H, s), 0.68(6H, s), 0.86(6H, s), 1.76(12H, s), 2.09(12H, s), 2.45(15H, s), 5.68(4H, s) | C: 59.31 H: 7.60 | C: 58.98 H: 7.58 |
| Example 8 {Me$_2$Si(2,3,5-Me$_3$Cp)$_2$Zr(C≡CPh)}$_2$O | 0.76(6H, s), 0.91(6H, s), 1.98(12H, s), 2.42(12H, s), 2.49(12H, s), 6.16(4H, s), 7.19~7.45(10H, m) | C: 66.36 H: 6.59 | C: 65.65 H: 6.71 |
| Example 9 {Me$_2$Si(2,3,5-Me$_3$Cp)$_2$Zr(C≡CSiMe$_3$)}$_2$O | 0.15(18H, s), 0.73(6H, s), 0.98(6H, s), 1.92(12H, s), 2.37(12H, s), 2.45(12H, s), 6.10(4H, s) | C: 59.20 H: 7.50 | C: 58.80 H: 7.60 |
| Example 10 {Me$_2$Si(2-(2-Furyl)-3,5-Me$_2$Cp)$_2$ZrCl}$_2$O | −0.09(6H, s) 1.05(6H, s), 2.28(12H, s), 2.55(12H, s) 6.17(8H, s), 6.45(4H, s), 7.13(4H, s) |  |  |

TABLE 2

Analytical data of Polypropylene

| Example | Amount of M used × 10$^{-6}$ mol | Yield g | Active kg-pp/ mmol-M-h | Mw × 10$^4$ | Mw/Mn | [η] | mmmm |
|---|---|---|---|---|---|---|---|
| Example 11 {Me$_2$Si(2,3,5-Me$_3$Cp)$_2$ZrCl}$_2$O | 1.61 | 7.2 | 4.5 | 7.31 | 2.45 | 0.61 | 0.196 |
| Example 13 {C$_4$H$_8$Si(2,3,5-Me$_3$Cp)$_2$ZrCl}$_2$O | 4.14 | 14.8 | 3.6 | 6.41 | 2.23 | 0.51 | 0.154 |
| Example 16 {Me$_2$Ge(2,3,5-Me$_3$Cp)$_2$ZrCl}$_2$O | 1.33 | 4.9 | 3.7 | 5.9 | 2.15 | 0.59 | 0.044 |
| Example 18 {Me$_2$Ge(2,3,5-Me$_3$Cp)$_2$HfCl}$_2$O | 4.91 | 1.7 | 0.35 | 20.0 | 2.32 | 1.59 | 0.153 |
| Example 20 {Me$_2$Si(2-(2-Furyl)-3,5-Me$_2$Cp)$_2$ZrCl}$_2$O | 0.42 | 0.38 | 0.9 | 24.4 | 1.74 | 1.62 | 0.073 |
| Comparative Example 1 (Cp$_2$ZrCl)$_2$O | 4.82 | 1.5 | 0.32 | 0.22 | 3.71 | 0.06 | 0.066 |

TABLE 3

Analytical data of Polyethylene

| Example | Amount of M used × 10$^{-6}$ mol | Yield g | Active kg-pp/ mmol-M-h | Mw × 10$^4$ | Mw/Mn | [η] | Tm °C. |
|---|---|---|---|---|---|---|---|
| Example 12 {Me$_2$Si(2,3,5-Me$_3$Cp)$_2$ZrCl}$_2$O | 0.47 | 20.2 | 86 | 10.1 | 2.03 | 2.00 | 135.8 |
| Example 14 {C$_4$H$_8$Si(2,3,5-Me$_3$Cp)$_2$ZrCl}$_2$O | 0.82 | 19.4 | 47 | 13.2 | 2.10 | 2.36 | 135.5 |
| Example 15 {Me$_2$Si(3-t-BuCp)$_2$ZrCl}$_2$O | 1.02 | 11.2 | 22 | 9.3 | 2.11 | 1.60 | 135.2 |
| Example 17 {Me$_2$Ge(2,3,5-Me$_3$Cp)$_2$ZrCl}$_2$O | 0.45 | 18.2 | 81 | 11.0 | 2.22 | 2.10 | 135.6 |

TABLE 3-continued

Analytical data of Polyethylene

| | Amount of M used × $10^{-6}$ mol | Yield g | Active kg-pp/ mmol-M-h | Mw × $10^4$ | Mw/Mn | [η] | Tm °C. |
|---|---|---|---|---|---|---|---|
| Example 19 {Me$_2$Ge(2,3,5-Me$_3$Cp)$_2$HfCl}$_2$O | 0.49 | 10.3 | 42 | 45.0 | 2.15 | 6.28 | 138.8 |

What is claimed is:

1. A α-oxo-bis-metallocene complex compound represented by the formula (1):

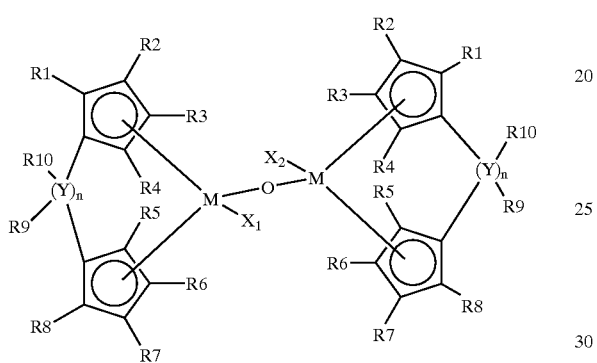

(1)

wherein M stands for a transition metal belonging to Group III, IV, V, VI, Lantanoid or Actinoid of the Periodic Table, n stands for an integer of 1 or 2, Y stands for carbon, silicon, germanium or tin, $X_1$ and $X_2$ may be the same or different and each independently stands for a halogen atom, a hologenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms, and nitrogen atoms in 5-membered or 6-membered ring or rings and which may be substituted on the ring or rings by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R2, R3, R6 and R7 are not hydrogen at the same time.

2. A μ-oxo-bis-metallocene complex compound according to claim 1, wherein M stands for titanium, zirconium or hafnium and Y stands for carbon, silicon or germanium.

3. A μ-oxo-bis-metallocene complex compound represented by the formula (2):

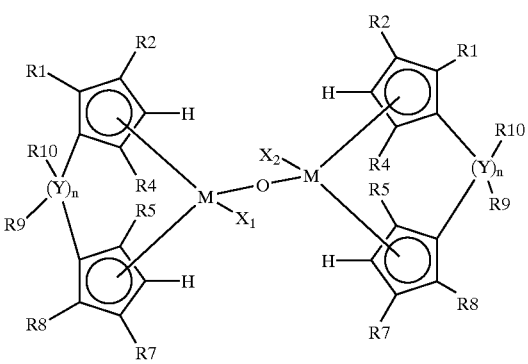

(2)

wherein M stands for titanium, zirconium, or hafnium, n stands for an integer of 1 or 2, Y stands for carbon, silicon, or germanium, $X_1$ and $X_2$ may be the same or different and each independently stands for a halogen atom, a halogenoid atomic group, a hydrocarbon group having 1–20 carbon atoms which may contain silicon, germanium, oxygen, sulfur, or nitrogen, or a monocyclic or polycyclic heteroaromatic which may contain a hetero atom or atoms selected from the group consisting of oxygen atoms, sulfur atoms and nitrogen atoms in 5-membered or 6-membered ring or rings and which may be substituted on the ring or rings by other substituents, R1, R2, R4, R5, R7 and R8 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that R1 and R2 may form together a cyclic structure having 5–8 carbon atoms and the cyclic structure may be an aromatic ring, that R7 and R8 may form a cyclic structure having 4–8 carbon atoms and which may contain oxygen, sulfur, and nitrogen, that R1, R2, R4, R5, R7 and R8 are not hydrogen at the same time, and that R2 and R7 are substituents other than hydrogen in which ligands coordinated to the two M's are commonly in meso position.

4. A catalyst for the polymerization of olefins which comprises, as essential components thereof, at least one 1-oxo-bis-metallocene complex compound represented by the formula (1):

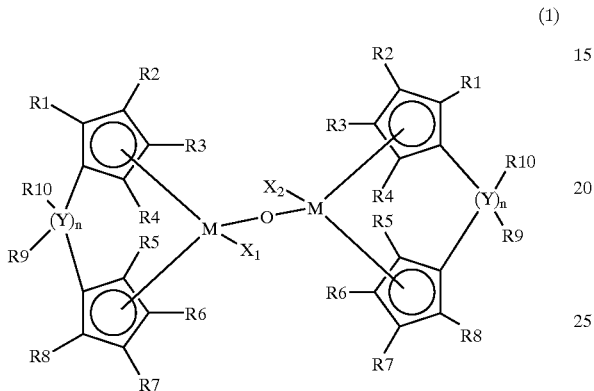

wherein M stands for a transition metal belonging to Group III, IV, V, VI, Lantanoid or Actinoid of the Periodic Table, n stands for an integer of 1 or 2, Y stands for carbon, silicon, germanium or tin, $X_1$ and $X_2$ may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R1–R8 are not hydrogen at the same time, and at least one cocatalyst selected from the group consisting of an aluminoxane, an ionic compound, and a Lewis acid.

5. A catalyst for the polymerization of olefins which comprises at least one μ-oxo-bis-metallocene complex compound represented by the formula (2):

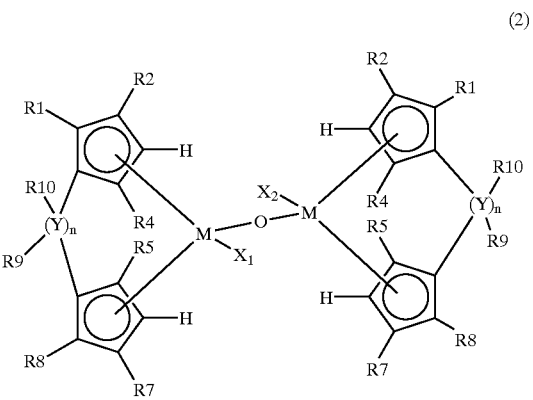

wherein M stands for titanium, zirconium, or hafnium, n stands for an integer of 1 or 2, Y stands for carbon, silicon, or germanium, $X_1$ and $X_2$ may be the same or different and each independently stands for a halogen atom, a halogenoid atomic group, a hydrocarbon group having 1–20 carbon atoms which may contain silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents, R1, R2, R4, R5, R7 and R8 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that R1 and R2 may form together a cyclic structure having 5–8 carbon atoms and the cyclic structure may be an aromatic ring, that R7 and R8 may form a cyclic structure having 4–8 carbon atoms and which may contain oxygen, sulfur and nitrogen, and that R1, R2, R4, R5, R7 and R8 are not hydrogen at the same time, and at least one cocatalyst selected from the group consisting of an aluminoxane, an ionic compound, and a Lewis acid.

6. A catalyst for the polymerization of olefins which comprises at least one μ-oxo-bis-metallocene complex compound represented by the formula (1):

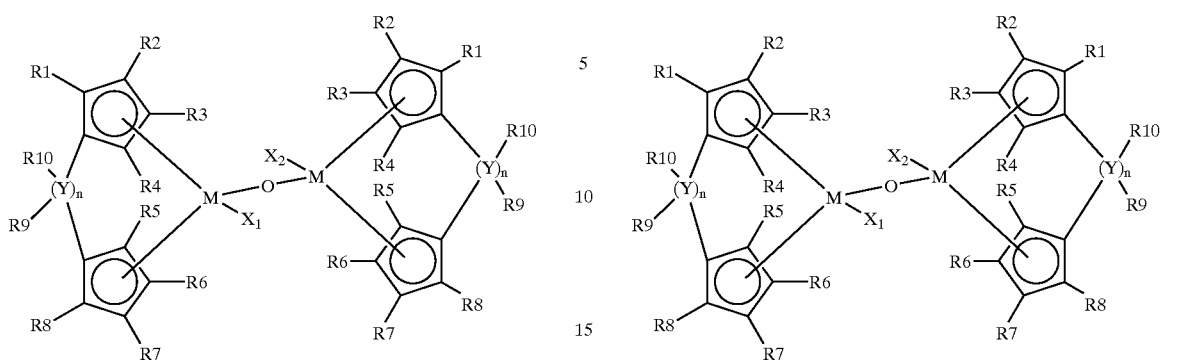

(1)

wherein M stands for a transition metal belonging to Group III, IV, V, VI, Lantanoid or Actinoid of the Periodic Table, n stands for an integer of 1 or 2, Y stands for carbon, silicon, germanium or tin, $X_1$ and $X_2$ may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents., R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or. a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R1–R8 are not hydrogen at the same time, and an aluminoxane as cocatalyst.

7. A process for the polymerization of olefins in the presence of a catalyst for the polymerization of olefins which comprises, as essential components thereof, at least one μ-oxo-bis-metallocene complex compound represented by the formula (1):

wherein M stands for a transition metal belonging to Group III, IV, V, VI, Lantanoid or Actinoid of the Periodic Table, n stands for an integer of 1 or 2, Y stands for carbon, silicon, germanium or tin, $X_1$ and $X_2$ may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R1–R8 are not hydrogen at the same time, and at least one cocatalyst selected from the group consisting of an aluminoxane, an ionic component, and a Lewis acid.

8. A catalyst for the polymerization of olefins according to claim 5, wherein the cocatalyst is an aluminoxane.

9. A process for the polymerization of olefins in the presence of the catalyst for the polymerization of olefins according to claim 5.

10. A process for the polymerization of olefins in the presence of a catalyst for the polymerization of olefins which comprises, as essential components thereof, at least one μ-oxo-bis-metallocene complex compound represented by the formula (1):

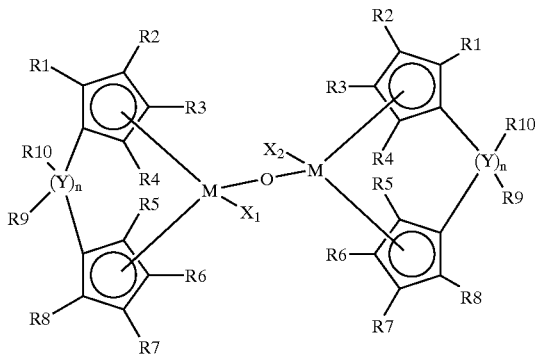

wherein M stands for a transition metal belonging to Group III, IV, V, VI, Lantanoid or Actinoid of the Periodic Table, n stands for an integer of 1 or 2, Y stands for carbon, silicon, germanium or tin, $X_1$ and $X_2$ may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in 5-membered or 6-membered ring or rings and which may be substituted on the ring or rings by other substituents with the proviso that adjacent substituents on the cyclopentadienyl groups may form together a cyclic structure having 5–8 carbon atoms and the cyclic structure may be an aromatic ring, that R9 and R10 may form together with Y a cyclic structure having 4–8 carbon atoms and which may contain oxygen, sulfur and nitrogen, and that R1–R8 are not hydrogen at the same time, and an aluminoxane as a cocatalyst.

11. A process for the polymerization of olefins in the presence of the catalyst for the polymerization of olefms according to claim 8.

12. A catalyst for the polymerization of olefins according to claim 4, wherein R2, R3, R6 and R7 are not hydrogen at the same time.

* * * * *